(12) United States Patent
Kronenthal et al.

(10) Patent No.: US 11,160,899 B2
(45) Date of Patent: Nov. 2, 2021

(54) INTRAOPERATIVE USES OF SETTABLE SURGICAL COMPOSITIONS

(71) Applicant: Abyrx, Inc., Irvington, NY (US)

(72) Inventors: Richard L. Kronenthal, Irvington, NY (US); Aniq Darr, Irvington, NY (US); John Pacifico, Irvington, NY (US)

(73) Assignee: Abyrx, Inc., Irvington, NY (US)

( * ) Notice: Subject to any disclaimer, the term of this patent is extended or adjusted under 35 U.S.C. 154(b) by 86 days.

(21) Appl. No.: 16/183,221

(22) Filed: Nov. 7, 2018

(65) Prior Publication Data

US 2019/0134259 A1    May 9, 2019

Related U.S. Application Data

(60) Provisional application No. 62/582,539, filed on Nov. 7, 2017.

(51) Int. Cl.
| | | |
|---|---|---|
| *A61L 24/02* | (2006.01) |
| *A61L 24/04* | (2006.01) |
| *A61L 24/00* | (2006.01) |
| *A61L 27/42* | (2006.01) |
| *A61L 27/18* | (2006.01) |
| *A61L 27/44* | (2006.01) |
| *A61L 27/46* | (2006.01) |
| *A61L 27/16* | (2006.01) |

(Continued)

(52) U.S. Cl.
CPC ......... *A61L 24/043* (2013.01); *A61L 24/0005* (2013.01); *A61L 24/0015* (2013.01); *A61L 24/0042* (2013.01); *A61L 24/02* (2013.01); *A61L 27/16* (2013.01); *A61L 27/18* (2013.01); *A61L 27/427* (2013.01); *A61L 27/44* (2013.01); *A61L 27/46* (2013.01); *A61L 2300/412* (2013.01); *A61L 2300/604* (2013.01); *A61L 2400/06* (2013.01); *A61L 2430/02* (2013.01); *A61L 2430/38* (2013.01); *C08L 33/12* (2013.01); *C08L 75/04* (2013.01)

(58) Field of Classification Search
CPC .... A61L 24/0042; A61L 24/043; A61L 24/02; A61L 24/0005; A61L 24/0015; A61B 17/8805; A61F 2/4601
See application file for complete search history.

(56) References Cited

U.S. PATENT DOCUMENTS

| | | | |
|---|---|---|---|
| 3,700,628 | A | 10/1972 | Dermody et al. |
| 3,924,640 | A | 12/1975 | King |

(Continued)

FOREIGN PATENT DOCUMENTS

WO    WO-2004/009227 A2    1/2004

OTHER PUBLICATIONS

Babst, et al. "Definitions and explanations on the topic of fracture reduction." Springer. Unfallchirurg. Feb. 2019;122(2):88-94. doi: 10.1007/s00113-018-0573-9.

*Primary Examiner* — Brian E Pellegrino
(74) *Attorney, Agent, or Firm* — Cooley LLP; Ivor R. Elrifi; Matthew Pavao

(57) ABSTRACT

Provided herein are bio-absorbable, settable and homogenous multi-putty bone-adhesive compositions for medical use in tissue hemostasis, surgical repair and reconstruction. Also provided are improved methods of intraoperative use of said compositions for re-approximation of adjacent bone fragments to create a restored alignment and stabilize fracture line.

28 Claims, 8 Drawing Sheets

(51) Int. Cl.
*C08L 33/12* (2006.01)
*C08L 75/04* (2006.01)

(56) References Cited

U.S. PATENT DOCUMENTS

| | | | |
|---|---|---|---|
| 4,829,099 | A | 5/1989 | Fuller et al. |
| 6,306,177 | B1 | 10/2001 | Felt et al. |
| 7,772,352 | B2 | 8/2010 | Bezwada |
| 7,964,207 | B2 | 6/2011 | Deslauriers et al. |
| 7,985,414 | B2 | 7/2011 | Knaack et al. |
| 8,002,843 | B2 | 8/2011 | Knaack et al. |
| 8,282,953 | B2 | 10/2012 | Drapeau et al. |
| 8,337,497 | B2 | 12/2012 | Deslauriers et al. |
| 8,431,147 | B2 | 4/2013 | Drapeau et al. |
| 8,506,983 | B2 | 8/2013 | Mohan et al. |
| 2001/0018614 | A1* | 8/2001 | Bianchi .............. A61L 24/0005 623/16.11 |
| 2005/0013793 | A1 | 1/2005 | Beckman et al. |
| 2007/0027230 | A1* | 2/2007 | Beyar .................. A61L 24/043 523/117 |
| 2009/0082540 | A1 | 3/2009 | Bezwada |
| 2012/0035610 | A1 | 2/2012 | Deslauriers et al. |
| 2012/0308552 | A1 | 12/2012 | Lally et al. |
| 2013/0236513 | A1 | 9/2013 | Guelcher et al. |
| 2016/0250374 | A1 | 9/2016 | Bezwada et al. |

\* cited by examiner

INTRAOPERATIVE USES OF SETTABLE SURGICAL COMPOSITIONS

RELATED APPLICATIONS

This application claims priority to U.S. Patent Application No. 62/582,539, filed Nov. 7, 2017, the contents of which are herein incorporated by reference in their entirety.

FIELD OF THE INVENTION

The present disclosure relates to the field of medical implants, particularly settable, implantable compositions for medical use in tissue hemostasis, repair and reconstruction.

BACKGROUND

Biodegradable polymers have become increasingly important for a variety of biomedical applications including biomedical implants, such as stents, and coatings applied to those implants, tissue engineering scaffolds, and soft-tissue adhesives. Segmented polyurethane elastomers in particular have come into wide use as biomaterials due to their superior mechanical properties and, chemical versatility. PCT International Application Publication No. WO 2004009227 describes certain degradable polyurethane compositions for use as tissue engineering scaffolds. U.S. Pat. No. 6,306,177 (Felt et al.) describes curable polyurethane compositions comprising a plurality of parts capable of being sterilized, stably stored, and mixed at the time of use in order to provide a flowable composition upon mixing that is sufficiently flowable to permit it to be delivered to the body by minimally invasive means. U.S. Patent Application Publication No. 20050013793 (Beckman et al.) also describes degradable polyurethanes for e.g., tissue engineering and particularly for bone repair and replacement. U.S. Pat. No. 4,829,099 (Fuller et al.) describes certain absorbable polyisocyanates for use as surgical adhesives. U.S. Pat. Nos. 8,002,843 and 7,985,414 (Knaack et al.) describe a biodegradable polyisocyanate (such as lysine diisocyanate) with an optionally hydroxylated biomolecule to form a degradable polyurethane. U.S. Pat. No. 7,964,207 (Deslaurier et al.) and U.S. Pat. No. 7,772,352 (Bezwada) describe osteoconductive polyurethane compositions having mechanical properties consistent for use in bone repair, including certain surgical procedures, e.g., as described in U.S. Pat. No. 8,337,497 (Deslaurier et al.).

For certain applications, in addition to being biodegradable, it is advantageous for a surgical implant to be moldable or formable, for example to optimize its placement at the implant site and/or to fill voids in hard or soft tissue at the site of implantation. U.S. Pat. Nos. 8,431,147 and 8,282,953 (Warsaw Orthopedic, Inc) describe malleable implants containing demineralized bone matrix. The "malleable implant compositions" described in these patents contain a particulate solid collagen material and a particulate solid DBM material along with a liquid carrier that comprises an aqueous gel of alginate. Alginate/DBM based compositions are also described in U.S. Pat. No. 8,506,983 (Warsaw Orthopedic, Inc). US 20130236513 (Guelcher et. al, Vanderbilt Univ.) describes polyurethane composites that, in some aspects, may be "processed" as a reactive liquid that subsequently cures in situ to form a solid composite.

There is a continuing need for improved surgical materials for use in hard and soft tissue repair.

SUMMARY OF THE INVENTION

The present disclosure relates to surgical putty materials and their intraoperative use in the context of tissue repair and/or reconstruction. These surgical putty materials can be used for repair and/or reconstitution of two or more pieces of bone, two or more pieces of cartilage, and/or two or more pieces of bone and cartilage.

In embodiments, the disclosure provides methods for joining pieces of cut or fractured bone, the methods comprising intraoperatively mixing two or more individual reactive putties to form a homogenous putty composition ("HPC"), optionally dividing the HPC into two or more additional portions, applying a first portion of the HPC to the cut or fractured surface of at least one of the pieces of bone, and maintaining the pieces of cut or fractured bone in proximity to form a reduced fracture until the HPC has hardened and the reduced fracture remains fixed. In embodiments, the first portion of the HPC is applied to the cut or fractured surface of at least one of the pieces of bone, either in multiple portions at a plurality of locations of the cut or fractured surface and interrupted by gaps, or as a single portion across substantially the entire length of the cut or fractured surface. In embodiments, the method further comprises compressing the pieces of cut or fractured bone together until the first portion of the HPC has hardened. In embodiments, the pieces of cut or fractured bone are maintained in proximity for about 2 to 5 minutes. In embodiments, the method further comprises applying a second portion of the HPC across the reduced fracture line in the form of a plate or tape. In embodiments, the method further comprises pressing additional portions of the HPC into each of two or more drill holes located opposite each other across the reduced fracture line, thereby substantially filling each drill hole. In embodiments, the method further comprises shaping an additional portion of the HPC into a rod and joining each end of the rod to a portion of HPC pressed into a drill hole. In embodiments, the method further comprises drilling a hole into the HPC material which is in the form of a plate or tape after the HPC has hardened.

In embodiments, the bone is a long bone, a short bone, a flat bone, an irregular bone, or a sesamoid bone. In embodiments (e.g., where the bone is a long bone or a short bone), the method further comprises stretching an additional portion of the HPC into the form of a ribbon or cuff and wrapping the HPC ribbon or cuff around the circumference of the reduced fracture line. In embodiments where the bone is a flat bone, the flat bone may be selected from a sternum, rib, scapula, or cranial bone. In embodiments where the bone is flat bone, the flat bone may be selected from a rib, scapula, or cranial bone. In embodiments where the bone is a rib bone, the method further comprises applying an additional portion of the HPC into the hollow of the rib bone.

In embodiments, the bone is an irregular bone. For example, the irregular bone is a vertebrae. In embodiments where the bone is a vertebrae, the method further comprises inserting an additional portion of the HPC into an intervertebral space to form a spacer or cage. In embodiments, the method further comprises applying a second portion of the HPC to two or more spinal pedicles adjacent to the HPC spacer or cage to form two or more HPC anchor points on the pedicles and either stretching a further portion of HPC between the anchor points or positioning a rod between the anchor points and pressing the rod into the anchor points, thereby connecting the anchor points.

In embodiments, the disclosure provides a method for joining at least two pieces (e.g., 2, 3, 4, 5, 6, 7, 8, 9, or more) of fractured long or short bone, the method comprising intraoperatively mixing together two or more individual reactive putties to form an HPC, dividing the HPC into at least two portions, applying a first portion of the HPC to the cut or fractured surface of at least one of the pieces of bone, maintaining the at least two pieces of cut or fractured bone in proximity to form a reduced fraction until the HPC has hardened sufficiently to maintain the reduced fracture repair fixed, shaping a second portion of HPC into the form of a ribbon or cuff and wrapping the HPC ribbon or cuff around the circumference of the reduced fracture line, optionally intraoperatively mixing two or more additional individual reactive putties to form one or more additional HPCs and using the one or more additional HPCs in one or more of the following further optional steps: shaping the one or more additional HPCs into one or more additional ribbons or cuffs and wrapping the one or more additional ribbons or cuffs around the circumference of the reduced fracture line, pressing portions of the one or more additional HPCs into each of two or more drill holes located opposite each other across the reduced fracture line, thereby substantially filling each drill hole, and/or shaping a portion of the one or more additional HPCs into a rod and joining each end of the rod to a portion of HPC pressed into a drill hole (e.g., by bending each end of the rod in order to fit it into a drill hole). In embodiments, such methods can be used to join shattered pieces of bone.

In embodiments, the disclosure provides a method for applying an internal orthopedic cast to a reapproximated long or short bone, the method comprising intraoperatively mixing two or more individual reactive putties to form an HPC, forming the HPC into the form of a ribbon or cuff, and wrapping the HPC ribbon or cuff around a circumference of reapproximated long or short bone.

In embodiments, the disclosure provides a method for spinal fusion, the method comprising intraoperatively mixing two or more individual reactive putties to form an HPC, optionally dividing the HPC into two or more additional portions, and inserting a first portion of the HPC into an intervertebral space to form a spacer or cage. In embodiments, the method further comprises introducing one or more of an autograft material, an allograft material, and/or a bone substitute material into one or more holes drilled into the HPC spacer or cage. In embodiments, the method further comprises applying a second portion of HPC to two or more spinal pedicles adjacent to the HPC spacer or cage to form two or more HPC anchor points on the pedicles and either stretching a further portion of HPC between the anchor points or positioning a rod between the anchor points and pressing the rod into the anchor points, thereby connecting the anchor points.

In embodiments, the disclosure provides a method for repair or reapproximation of bone fragments, the method comprising intraoperatively mixing two or more individual reactive putties to form an HPC, optionally dividing the HPC into two or more additional portions, applying a first portion of the HPC to one or more surfaces of a bone fragment and/or to the surface of a bone void to be filled by the fragment, and pressing the fragment into the void.

In embodiments, the disclosure provides a method for repair or reapproximation of bone fragments, the method comprising intraoperatively mixing two or more individual reactive putties to form an HPC, optionally dividing the HPC into two or more additional portions, applying a first portion of the HPC to one or more surfaces of a bone fragment and/or to the surface of a bone void to be filled by the fragment, and pressing the fragment into the void. In embodiments, the method further comprises applying a second portion of HPC across the reapproximated surface in the form of a plate or tape. In embodiments, the method further comprises pressing additional portions of the HPC into each of two or more drill holes located adjacent to each other, or opposite each other across the fracture line, thereby substantially filling each drill hole.

In embodiments, the disclosure provides a method for stabilizing surgical hardware, the method comprising intraoperatively mixing two or more individual reactive putties to form an HPC, optionally dividing the HPC into two or more additional portions, and applying a portion of HPC between the surface of a bone and the joint hardware, and/or by applying a portion of HPC across the surface of the joint hardware after it has been affixed to the bone.

In embodiments, the disclosure provides a method for stabilizing a surgical screw, the method comprising intraoperatively mixing two or more individual reactive putties to form an HPC, filling a drilled or tapped hole with a portion of HPC, and inserting the screw into the HPC before it hardens, or optionally, setting the screw into the HPC after it hardens.

In embodiments, the disclosure provides a method for repair of cartilaginous tissue, the method comprising intraoperatively mixing two or more individual reactive putties to form an HPC, and applying the HPC into a void or space formerly occupied by cartilaginous tissue in an amount sufficient to substantially fill the void or space.

The disclosure also provides an HPC for use in any of the methods described here, the HPC comprising 20-30 (e.g., 20-25, 25-30, for example, 20, 21, 22, 23, 24, 25, 26, 27, 28, 29, or 30) wt % of a polyurethane or polyurethane urea copolymer, optionally 60-75 (e.g., 60-65, 65-70, 70-75, for example, 60, 61, 62, 63, 64, 65, 66, 67, 68, 69, 70, 71, 72, 73, 74, or 75) wt % of a particulate material, and 4-10 (e.g., 4-6, 4-7, 4-8, 4-9, 5-7, 5-8, 5-9, 5-10, 6-8, 6-9, 6-10, 7-9, 7-10, or 8-10, for example, 4, 5, 6, 7, 8, 9, or 10) wt % of one or more additive materials, wherein the HPC is formed from mixing two individual reactive putties, wherein a first reactive putty comprises an isocyanate component (wherein the isocyanate component comprises a prepolymer (e.g., a low molecular weight polymer having reactive end groups) and/or a free polyisocyanate) and a second reactive putty comprises a polyol and/or a polyamine component (wherein the polyol/polyamine component comprises a prepolymer (e.g., a low molecular weight polymer having reactive end groups) and/or free polyol and/or polyamine), respectively, and each putty independently further comprising an optional particulate component and wherein, when the optional particulate component is present, the prepolymer is present in an amount of from about 2-10 (e.g., 2-4, 2-5, 2-6, 2-7, 2-8, 2-9, 2-10, 3-5, 3-6, 3-7, 3-8, 3-9, 3-10, 4-6, 4-7, 4-8, 4-9, 4-10, 5-7, 5-8, 5-9, 5-10, 6-8, 6-9, 6-10, 7-9, 7-10, 8-10, for example, 2, 3, 4, 5, 6, 7, 8, 9, or 10) wt %, preferably about 5-7 (e.g., 5, 6, or 7) wt %, or about 3-8 (e.g., 3, 4, 5, 6, 7, or 8) wt % of each individual reactive putty; and wherein, when the optional particulate component is absent, the prepolymer is present in an amount of from about 15-50 (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) wt % or about 20-50 (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) wt % or about 25-50 (e.g., 25, 26, 27, 28, 29, 30, 31, 32, 33, 34, 35, 36, 37, 38, 39, 40, 41, 42, 43, 44, 45, 46, 47, 48, 49, or 50), about 30-50 (e.g., 30, 31, 32, 33, 34, 35, 36, 37, 38, 39, 40, 41, 42, 43, 44, 45, 46, 47, 48, 49, or 50), about 35-50 (e.g., 35, 36, 37, 38, 39, 40, 41, 42, 43, 44, 45, 46, 47, 48, 49, or 50), about 40-50 (e.g., 40, 41, 42, 43, 44, 45, 46, 47, 48, 49, or 50), about 45-50 (e.g., 45, 46, 47, 48, 49, or 50), 20-45 (e.g., 20, 21, 22, 23, 24, 25, 26, 27, 28, 29, 30, 31, 32, 33, 34, 35, 36, 37, 38, 39, 40, 41, 42, 43, 44, 45), 20-40 (e.g., 20, 21, 22, 23, 24, 25, 26, 27, 28, 29, 30, 31, 32, 33, 34, 35, 36, 37, 38, 39, or 40), 20-35 (e.g., 20, 21, 22, 23, 24, 25, 26, 27, 28, 29, 30, 31, 32, 33, 34, or 35), 20-30 (e.g., 20, 21, 22, 23, 24, 25, 26, 27, 28, 29, or 30), 25-45 (e.g., 25, 26, 27, 28, 29, 30, 31, 32, 33, 34, 35, 36, 37, 38, 39, 40, 41, 42, 43, 44, or 45), 25-40 (e.g., 25, 26, 27, 28, 29, 30, 31, 32, 33, 34, 35, 36, 37, 38, 39, or 40), 25-35 (e.g., 25, 26, 27, 28, 29, 30, 31, 32, 33, 34, or 35), 25-30 (e.g., 25, 26, 27, 28, 29, or 30), 30-45 (e.g., 30, 31, 32, 33, 34, 35, 36, 37, 38, 39, 40, 41, 42, 43, 44, or 45), 30-40 (e.g., 35, 36, 37, 38, 39, or 40), 30-35 (e.g., 30, 31, 32, 33, 34, or 35), 35-45 (e.g., 35, 36, 37, 38, 39, 40, 41, 42, 43, 44, or 45), 35-40 (e.g., 35, 36, 37, 38, 39, or 40), or 40-45 (e.g., 40, 41, 42, 43, 44, or 45) wt % of each individual reactive putty.

In any of the methods described herein, the HPC may comprise 20-30 (e.g., 20-25, 25-30, for example, 20, 21, 22, 23, 24, 25, 26, 27, 28, 29, or 30) wt % of a polyurethane or polyurethane urea copolymer, optionally 60-75 (e.g., 60-65, 65-70, 70-75, for example, 60, 61, 62, 63, 64, 65, 66, 67, 68, 69, 70, 71, 72, 73, 74, or 75) wt % of a particulate material, and 4-10 (e.g., 4-6, 4-7, 4-8, 4-9, 5-7, 5-8, 5-9, 5-10, 6-8, 6-9, 6-10, 7-9, 7-10, or 8-10, for example, (4, 5, 6, 7, 8, 9, or 10) wt % of one or more additive materials, wherein a first reactive putty comprises: (i) an isocyanate component (wherein the isocyanate component comprises a prepolymer (e.g., a low molecular weight polymer having reactive end groups) and/or a free polyisocyanate) and a second reactive putty comprises (ii) a polyol component, a polyamine component, or both a polyol component and a polyamine component (wherein the polyol and/or polyamine component comprises a prepolymer (e.g., a low molecular weight polymer having reactive end groups) and/or free polyol and/or polyamine), wherein each reactive putty independently further comprises an optional particulate component. In embodiments, when the optional particulate component is present, the prepolymer is present in an amount of from about 2-10 (e.g., 2-4, 2-5, 2-6, 2-7, 2-8, 2-9, 2-10, 3-5, 3-6, 3-7, 3-8, 3-9, 3-10, 4-6, 4-7, 4-8, 4-9, 4-10, 5-7, 5-8, 5-9, 5-10, 6-8, 6-9, 6-10, 7-9, 7-10, 8-10, for example, 2, 3, 4, 5, 6, 7, 8, 9, or 10) wt % of each individual reactive putty. In embodiments, when the prepolymer is present in an amount of about 5-7 (e.g., 5, 6, or 7) wt % or about 3-8 (e.g., 3, 4, 5, 6, 7, or 8) wt % of each individual reactive putty. In embodiments, the optional particulate component is absent, the prepolymer is present in an amount of from about (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) wt % or about 20-50 (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) wt % or about 25-50 (e.g., 25, 26, 27, 28, 29, 30, 31, 32, 33, 34, 35, 36, 37, 38, 39, 40, 41, 42, 43, 44, 45, 46, 47, 48, 49, or 50), about 30-50 (e.g., 30, 31, 32, 33, 34, 35, 36, 37, 38, 39, 40, 41, 42, 43, 44, 45, 46, 47, 48, 49, or 50), about 35-50 (e.g., 35, 36, 37, 38, 39, 40, 41, 42, 43, 44, 45, 46, 47, 48, 49, or 50), about 40-50 (e.g., 40, 41, 42, 43, 44, 45, 46, 47, 48, 49, or 50), about 45-50 (e.g., 45, 46, 47, 48, 49, or 50), 20-45 (e.g., 20, 21, 22, 23, 24, 25, 26, 27, 28, 29, 30, 31, 32, 33, 34, 35, 36, 37, 38, 39, 40, 41, 42, 43, 44, 45), 20-40 (e.g., 20, 21, 22, 23, 24, 25, 26, 27, 28, 29, 30, 31, 32, 33, 34, 35, 36, 37, 38, 39, or 40), 20-35 (e.g., 20, 21, 22, 23, 24, 25, 26, 27, 28, 29, 30, 31, 32, 33, 34, or 35), 20-30 (e.g., 20, 21, 22, 23, 24, 25, 26, 27, 28, 29, or 30), 25-45 (e.g., 25, 26, 27, 28, 29, 30, 31, 32, 33, 34, 35, 36, 37, 38, 39, 40, 41, 42, 43, 44, or 45), 25-40 (e.g., 25, 26, 27, 28, 29, 30, 31, 32, 33, 34, 35, 36, 37, 38, 39, or 40), 25-35 (e.g., 25, 26, 27, 28, 29, 30, 31, 32, 33, 34, or 35), 25-30 (e.g., 25, 26, 27, 28, 29, or 30), 30-45 (e.g., 30, 31, 32, 33, 34, 35, 36, 37, 38, 39, 40, 41, 42, 43, 44, or 45), 30-40 (e.g., 35, 36, 37, 38, 39, or 40), 30-35 (e.g., 30, 31, 32, 33, 34, or 35), 35-45 (e.g., 35, 36, 37, 38, 39, 40, 41, 42, 43, 44, or 45), 35-40 (e.g., 35, 36, 37, 38, 39, or 40), or 40-45 (e.g., 40, 41, 42, 43, 44, or 45) wt % of each individual reactive putty.

In embodiments, the particulate component comprises spherical particles of calcium phosphate in a size range of from about 1-700 microns mean diameter and a density in the range of 2-3 g/cm$^3$. In embodiments, the calcium phosphate particles consist of particles selected from one or more of tricalcium phosphate (TCP), tetracalcium phosphate, calcium pyrophosphate, hydroxyapatite, siliconized calcium phosphate, and a substituted calcium phosphate where the substitution is with magnesium, strontium, or silicate. In embodiments, the calcium phosphate particles consist of particles selected from one or more of tricalcium phosphate and hydroxyapatite. In embodiments, the particulate component comprises particles of calcium sulfate, bone, partially or fully demineralized bone matrix (DBM), mineralized bone, and/or combinations of the foregoing. In embodiments, the particulate component comprises particles of bone in the form of demineralized bone, allograft bone, and/or autogenous bone. In embodiments, the particulate component comprises a ceramic material such as substituted calcium phosphates or a glass, or bioglass.

In embodiments, the one or more additive materials is selected from one or more of a carboxylic acid ester of glycerin, a divalent metal salt of a fatty acid, the acetic acid ester of tocopherol, an N-alkylpyrrolidone, and triethanolamine. In embodiments, the one or more additive materials comprises one or more therapeutic agent selected from an anti-cancer agent, an antimicrobial agent, an antibiotic, a local anesthetic or analgesic, a statin and an anti-inflammatory agent.

In embodiments, the HPC exhibits a stiffness in the range of about 4-6 (e.g., 4, 5, or 6) millimeters for at least about 2 minutes after its formation when subjected to a penetrometer test using a force of about 50 grams applied for about 5 seconds. In embodiments, the HPC exhibits a stiffness in the range of about 0.2-0.4 (e.g., 0.2, 0.3, 0.4) millimeters about 15 minutes after its formation when subjected to a penetrometer test using a force of about 50 grams applied for about 5 seconds.

In embodiments, the HPC is sterile.

In embodiments, the HPC is fully or partially biodegradable and/or bioabsorbable under physiological conditions.

The disclosure also provides an HPC for use in any of the methods disclosed herein, wherein the HPC comprises a cyanoacrylate adhesive composition, wherein the first individual reactive putty comprises 20-50 wt % (e.g., 25-50, 30-50, 35-50, 40-50, 45-50, 30-35, 30-40, 30-45, 35-40, 35-45, 40-45, for example, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50%) of an alkyl cyanoacrylate monomer (based on the weight of the first putty), 1-15 wt % (e.g., 1-5, 1-10, 5-10, 5-15, 10-15, for example, 1, 2, 3, 4, 5, 6, 7, 8, 9, 10, 11, 12, 13, 14, or 15%) of a poly(alkylcyanoacrylate) as a viscosity enhancer (based on the weight of the first putty), 1-2 wt (e.g., 1-1.5, 1.5-2, for example, 1, 1.1, 1.2, 1.3, 1.4, 1.5, 1.6, 1.7, 1.8, 1.9, or 2%) of a free radical-induced polymerization inhibitor (based on the weight of the first putty), and 0.5-2 wt (e.g., 0.5-1, 0.5-1.5, 1-1.5, 1-2, 1.5-2, for example, 0.5 0.6, 0.7, 0.8, 0.9, 1.0, 1.1, 1.2, 1.3, 1.4, 1.5, 1.6, 1.7, 1.8, 1.9, or 2%) of a base catalyzed polymerization inhibitor (based on the weight of the first putty), wherein the second individual reactive putty comprises 3-40 wt % (e.g., 3-5, 3-10, 3-15, 3-20, 3-25, 3-30, 3-35, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40%) of poly(alkylcyanoacrylate) as a viscosity enhancer (based on the weight of the second putty), 0-85 wt % (e.g, 0-80, 0-75, 0-70, 0-65, 0-60, 0-55, 0-50, 0-45, 0-40, 0-35, 0-30, 0-25, 0-20, 0-15, 0-10, 0-5, 5-85, 5-80, 5-75, 5-70, 5-65, 5-60, 5-55, 5-50, 5- 45, 5-40, 5-35, 5-30, 5-25, 5-20, 5-15, 5-10, 10-85, 10-80, 10-75, 10-70, 10-65, 10-60, 10-55, 10-50, 10-45, 10-40, 10-35, 10-30, 10-25, 10-20, 10-15, 15-85, 15-80, 15-75, 15-70, 15-65, 15-60, 15-55, 15-50, 15-45, 15-40, 15-35, 15-30, 15-25, 15-20, 20-85, 20-80, 20-75, 20-70, 20-65, 20-60, 20-55, 20-50, 20-45, 20-40, 20-35, 20-30, 20-25, 25-85, 25-80, 25-75, 25-70, 25-65, 25-60, 25-55, 25-50, 25-45, 25-40, 25-35, 25-30, 30-85, 30-80, 30-75, 30-70, 30-65, 30-60, 30-55, 30-50, 30-45, 30-40, 30-35, 35-85, 35-80, 35-75, 35-70, 35-65, 35-60, 35-55, 35-50, 35-45, 35-40, 40-85, 40-80, 40-75, 40-70, 40-65, 40-60, 40-55, 40-50, 40-45, 45-85, 45-80, 45-75, 45-70, 45-65, 45-60, 45-55, 45-50, 50-85, 50-80, 50-75, 50-70, 50-65, 50-60, 55-85, 55-80, 55-75, 55-70, 55-65, 55-60, 60-85, 60-80, 60-75, 60-70, 60-65, 65-86, 65-80, 65-75, 65-70, 70-85, 70-80, 70-75, 75-85, or 75-80, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85%) of a particulate material (based on the weight of the second putty), and 0-40 wt (e.g., 0-40, 0-35, 0-30, 0-25, 0-20, 0-15, 0-10, 0-5, 5-40, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35, or 35-40, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40% of materials selected from the group consisting of therapeutic and growth-promoting agents (based on the weight of the second putty), and wherein the first and second reactive putties are intraoperatively mixed by hand-mixing or kneading to form the HPC.

In any of the methods described herein, the HPC may comprise a cyanoacrylate adhesive composition, wherein the first individual reactive putty comprises 20-50 wt (e.g., 25-50, 30-50, 35-50, 40-50, 45-50, 30-35, 30-40, 30-45, 35-40, 35-45, 40-45, for example, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50%) of an alkyl cyanoacrylate monomer (based on the weight of the first putty), 1-15 wt % (e.g., 1-5, 1-10, 5-10, 5-15, 10-15, for example, 1, 2, 3, 4, 5, 6, 7, 8, 9, 10, 11, 12, 13, 14, or 15%) of a poly(alkylcyanoacrylate) as a viscosity enhancer (based on the weight of the first putty), 1-2 wt % (e.g, 1-1.5, 1.5-2, for example, 1, 1.1, 1.2, 1.3, 1.4, 1.5, 1.6, 1.7, 1.8, 1.9, or 2%) of a free radical-induced polymerization inhibitor (based on the weight of the first putty), and 0.5-2 wt % (e.g., 0.5-1, 0.5-1.5, 1-1.5, 1-2, 1.5-2, for example, 0.5 0.6, 0.7, 0.8, 0.9, 1.0, 1.1, 1.2, 1.3, 1.4, 1.5, 1.6, 1.7, 1.8, 1.9, or 2%) of a base catalyzed polymerization inhibitor (based on the weight of the first putty), wherein the second individual reactive putty comprises 3-40 wt (e.g., 3-5, 3-10, 3-15, 3-20, 3-25, 3-30, 3-35, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40%) of poly(alkylcyanoacrylate) as a viscosity enhancer (based on the weight of the second putty), 0-85 wt % (0-80, 0-75, 0-70, 0-65, 0-60, 0-55, 0-50, 0-45, 0-40, 0-35, 0-30, 0-25, 0-20, 0-15, 0-10, 0-5, 5-85, 5-80, 5-75, 5-70, 5-65, 5-60, 5-55, 5-50, 5-45, 5-40, 5-35, 5-30, 5-25, 5-20, 5-15, 5-10, 10-85, 10-80, 10-75, 10-70, 10-65, 10-60, 10-55, 10-50, 10-45, 10-40, 10-35, 10-30, 10-25, 10-20, 10-15, 15-85, 15-80, 15-75, 15-70, 15-65, 15-60, 15-55, 15-50, 15-45, 15-40, 15-35, 15-30, 15-25, 15-20, 20-85, 20-80, 20-75, 20-70, 20-65, 20-60, 20-55, 20-50, 20-45, 20-40, 20-35, 20-30, 20-25, 25-85, 25-80, 25-75, 25-70, 25-65, 25-60, 25-55, 25-50, 25-45, 25-40, 25-35, 25-30, 30-85, 30-80, 30-75, 30-70, 30-65, 30-60, 30-55, 30-50, 30-45, 30-40, 30-35, 35-85, 35-80, 35-75, 35-70, 35-65, 35-60, 35-55, 35-50, 35-45, 35-40, 40-85, 40-80, 40-75, 40-70, 40-65, 40-60, 40-55, 40-50, 40-45, 45-85, 45-80, 45-75, 45-70, 45-65, 45-60, 45-55, 45-50, 50-85, 50-80, 50-75, 50-70, 50-65, 50-60, 50-55, 55-85, 55-80, 55-75, 55-70, 55-65, 55-60, 60-85, 60-80, 60-75, 60-70, 60-65, 65-86, 65-80, 65-75, 65-70, 70-85, 70-80, 70-75, 75-85, or 75-80, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85%) of a particulate material (based on the weight of the second putty), and 0-40 wt (e.g., 0-40, 0-35, 0-30, 0-25, 0-20, 0-15, 0-10, 0-5, 5-40, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35, or 35-40, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40% of materials selected from the group consisting of therapeutic and growth-promoting agents (based on the weight of the second putty), and wherein the first and second reactive putties are intraoperatively mixed by hand-mixing or kneading to form the HPC.

In embodiments, the free radical-induced polymerization inhibitor is hydroquinone.

In embodiments, the base catalyzed polymerization inhibitor is sulfur dioxide.

The disclosure also provides an HPC for use in any of the methods described herein, wherein the HPC comprises a methylidene malonate alkyldiester adhesive composition wherein the first individual reactive putty comprises a dialkyl methylidene malonate monomer, 3-40 wt % (e.g., 3-5, 3-10, 3-15, 3-20, 3-25, 3-30, 3-35, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40%) of a poly(methylidene malonate diester) as a viscosity enhancer (based on the weight of the first putty), 0-85 wt % (0-80, 0-75, 0-70, 0-65, 0-60, 0-55, 0-50, 0-45, 0-40, 0-35, 0-30, 0-25, 0-20, 0- 15, 0-10, 0-5, 5-85, 5-80, 5-75, 5-70, 5-65, 5-60, 5-55, 5-50, 5-45, 5-40, 5-35, 5-30, 5-25, 5-20, 5-15, 5-10, 10-85, 10-80, 10-75, 10-70, 10-65, 10-60, 10-55, 10-50, 10-45, 10-40, 10-35, 10-30, 10-25, 10-20, 10-15, 15-85, 15-80, 15-75, 15-70, 15-65, 15-60, 15-55, 15-50, 15-45, 15-40, 15-35, 15-30, 15-25, 15-20, 20-85, 20-80, 20-75, 20-70, 20-65, 20-60, 20-55, 20-50, 20-45, 20-40, 20-35, 20-30, 20-25, 25-85, 25-80, 25-75, 25-70, 25-65, 25-60, 25-55, 25-50, 25-45, 25-40, 25-35, 25-30, 30-85, 30-80, 30-75, 30-70, 30-65, 30-60, 30-55, 30-50, 30-45, 30-40, 30-35, 35-85, 35-80, 35-75, 35-70, 35-65, 35-60, 35-55, 35-50, 35-45, 35-40, 40-85, 40-80, 40-75, 40-70, 40-65, 40-60, 40-55, 40-50, 40-45, 45-85, 45-80, 45-75, 45-70, 45-65, 45-60, 45-55, 45-50, 50-85, 50-80, 50-75, 50-70, 50-65, 50-60, 50-55, 55-85, 55-80, 55-75, 55-70, 55-65, 55-60, 60-85, 60-80, 60-75, 60-70, 60-65, 65-86, 65-80, 65-75, 65-70, 70-85, 70-80, 70-75, 75-85, or 75-80, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85%) of a particulate material (based on the weight of the first putty), 1-2 wt % (e.g., 1-1.5, 1.5-2, for example, 1, 1.1, 1.2, 1.3, 1.4, 1.5, 1.6, 1.7, 1.8, 1.9, or 2%) of a free radical-induced polymerization inhibitor (based on the weight of the first putty), and 0.5-2 wt % (e.g., 0.5-1, 0.5-1.5, 1-1.5, 1-2, 1.5-2, for example, 0.5 0.6, 0.7, 0.8, 0.9, 1.0, 1.1, 1.2, 1.3, 1.4, 1.5, 1.6, 1.7, 1.8, 1.9, or 2%) a base catalyzed polymerization inhibitor (based on the weight of the first putty), wherein the second individual reactive putty comprises 3-40 wt (e.g., 3-5, 3-10, 3-15, 3-20, 3-25, 3-30, 3-35, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40%) of a poly(methylidene malonate diester) as a viscosity enhancer (based on the weight of the second putty), 0-85 wt % (e.g., 0-80, 0-75, 0-70, 0-65, 0-60, 0-55, 0-50, 0-45, 0-40, 0-35, 0-30, 0-25, 0-20, 0-15, 0-10, 0-5, 5-85, 5- 80, 5-75, 5-70, 5-65, 5-60, 5-55, 5-50, 5-45, 5-40, 5-35, 5-30, 5-25, 5-20, 5-15, 5-10, 10-85, 10-80, 10-75, 10-70, 10-65, 10-60, 10-55, 10-50, 10-45, 10-40, 10-35, 10-30, 10-25, 10-20, 10-15, 15-85, 15-80, 15-75, 15-70, 15-65, 15-60, 15-55, 15-50, 15-45, 15-40, 15-35, 15-30, 15-25, 15-20, 20-85, 20-80, 20-75, 20-70, 20-65, 20-60, 20-55, 20-50, 20-45, 20-40, 20-35, 20-30, 20-25, 25-85, 25-80, 25-75, 25-70, 25-65, 25-60, 25-55, 25-50, 25-45, 25-40, 25-35, 25-30, 30-85, 30-80, 30-75, 30-70, 30-65, 30-60, 30-55, 30-50, 30-45, 30-40, 30-35, 35-85, 35-80, 35-75, 35-70, 35-65, 35-60, 35-55, 35-50, 35-45, 35-40, 40-85, 40-80, 40-75, 40-70, 40-65, 40-60, 40-55, 40-50, 40-45, 45-85, 45-80, 45-75, 45-70, 45-65, 45-60, 45-55, 45-50, 50-85, 50-80, 50-75, 50-70, 50-65, 50-60, 50-55, 55-85, 55-80, 55-75, 55-70, 55-65, 55-60, 60-85, 60-80, 60-75, 60-70, 60-65, 65-86, 65-80, 65-75, 65-70, 70-85, 70-80, 70-75, 75-85, or 75-80, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85%) of a particulate material (based on the weight of the second putty), and 0-40 wt % (e.g., 0-40, 0-35, 0-30, 0-25, 0-20, 0-15, 0-10, 0-5, 5-40, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35, or 35-40, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40%) of materials selected from the group of therapeutic and of tissue growth-promoting agents (based on the weight of the second putty), and wherein the first and second reactive putties are intraoperatively mixed by hand-mixing or kneading to form the HPC.

In any of the methods described herein, the HPC may comprise a methylidene malonate alkyldiester adhesive composition wherein the first individual reactive putty comprises a dialkyl methylidene malonate monomer, 3-40 wt % (e.g., 3-5, 3-10, 3-15, 3-20, 3-25, 3-30, 3-35, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40%) of a poly(methylidene malonate diester) as a viscosity enhancer (based on the weight of the first putty), 0-85 wt % (e.g., 0-80, 0-75, 0-70, 0-65, 0-60, 0-55, 0-50, 0-45, 0-40, 0-35, 0-30, 0-25, 0-20, 0-15, 0-10, 0-5, 5-85, 5-80, 5-75, 5-70, 5-65, 5-60, 5-55, 5-50, 5-45, 5-40, 5-35, 5-30, 5-25, 5-20, 5-15, 5-10, 10-85, 10-80, 10-75, 10-70, 10-65, 10-60, 10-55, 10-50, 10-45, 10-40, 10-35, 10-30, 10-25, 10-20, 10-15, 15-85, 15-80, 15-75, 15-70, 15-65, 15-60, 15-55, 15-50, 15-45, 15-40, 15-35, 15-30, 15-25, 15-20, 20-85, 20-80, 20-75, 20-70, 20-65, 20-60, 20-55, 20-50, 20-45, 20-40, 20-35, 20-30, 20-25, 25-85, 25-80, 25-75, 25-70, 25-65, 25-60, 25-55, 25-50, 25-45, 25-40, 25-35, 25-30, 30-85, 30-80, 30-75, 30-70, 30-65, 30-60, 30-55, 30-50, 30-45, 30-40, 30-35, 35-85, 35-80, 35-75, 35-70, 35-65, 35-60, 35-55, 35-50, 35-45, 35-40, 40-85, 40-80, 40-75, 40-70, 40-65, 40-60, 40-55, 40-50, 40-45, 45-85, 45-80, 45-75, 45-70, 45-65, 45-60, 45-55, 45-50, 50-85, 50-80, 50-75, 50-70, 50-65, 50-60, 50-55, 55-85, 55-80, 55-75, 55-70, 55-65, 55-60, 60-85, 60-80, 60-75, 60-70, 60-65, 65-86, 65-80, 65-75, 65-70, 70-85, 70-80, 70-75, 75-85, or 75-80, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85%) of a particulate material (based on the weight of the second putty), and 0-40 wt (e.g., 0-40, 0-35, 0-30, 0-25, 0-20, 0-15, 0-10, 0-5, 5-40, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35, or 35-40, for example, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40%) of materials selected from the group of therapeutic and of tissue growth-promoting agents (based on the weight of the second putty), and wherein the first and second reactive putties are intraoperatively mixed by hand-mixing or kneading to form the HPC.

In embodiments, the free radical-induced polymerization inhibitor is hydroquinone.

In embodiments, the base catalyzed polymerization inhibitor is sulfur dioxide.

The disclosure also provides an HPC for use in any of the methods described herein, wherein the HPC comprises a magnesium phosphate-based bio-adhesive system and is formed from mixing two individual reactive putties, wherein the first individual reactive putty comprises 40-50 (e.g., 40-42, 40-43, 40-44, 40-45, 40-46, 40-47, 40-48, 40-49, 41-43, 41-44, 41-45, 41-46, 41-47, 41-48, 41-49, 41-50, 42-44, 42-45, 42-46, 42-47, 42-48, 42-49, 42-50, 43-45, 43-46, 43-47, 43-48, 43-49, 43-50, 44-46, 44-47, 44-48, 44-49, 44-50, 45-47, 45-48, 45-49, 45-50, 46-48, 46-49, 46-50, 47-49, 47-50, or 48-50, for example, 40, 41, 42, 43, 44, 45, 46, 47, 48, 49, or 50) wt % of potassium dihydrogen phosphate (based on the weight of the first putty), 35-50 (e.g., 35-45, 35-40, or 45-50, for example, 35, 36, 37, 38, 39, 40, 41, 42, 43, 44, 45, 46, 47, 48, 49, or 50) wt % of magnesium oxide (based on the weight of the first putty), and 10 wt % of $Ca_{10}(PO_4)_6(OH)_2$ suspended in an anhydrous, partially water miscible poloxamer (based on the weight of the first putty), and an optional viscosity-building agent, wherein the second individual reactive putty comprises an aqueous solution of a viscosity-building agent and, optionally, a particulate material, a colorant, and a therapeutic agent, and wherein the first and second reactive putties are intraoperatively mixed by hand-mixing or kneading to form the HPC.

In any of the methods described herein, the HPC may comprise a magnesium phosphate-based bio-adhesive system and is formed from mixing two individual reactive putties, wherein the first individual reactive putty comprises 40-50 (e.g., 40-42, 40-43, 40-44, 40-45, 40-46, 40-47, 40-48, 40-49, 41-43, 41-44, 41-45, 41-46, 41-47, 41-48, 41-49, 41-50, 42-44, 42-45, 42-46, 42-47, 42-48, 42-49, 42-50, 43-45, 43-46, 43-47, 43-48, 43-49, 43-50, 44-46, 44-47, 44-48, 44-49, 44-50, 45-47, 45-48, 45-49, 45-50, 46-48, 46-49, 46-50, 47-49, 47-50, or 48-50, for example, 40, 41, 42, 43, 44, 45, 46, 47, 48, 49, or 50) wt % of potassium dihydrogen phosphate (based on the weight of the first putty), 35-50 (e.g., 35-45, 35-40, or 45-50, for example, 35, 36, 37, 38, 39, 40, 41, 42, 43, 44, 45, 46, 47, 48, 49, or 50) wt % of magnesium oxide (based on the weight of the first putty), and 10 wt % of $Ca_{10}(PO_4)_6(OH)_2$ (based on the weight of the first putty) suspended in an anhydrous, partially water miscible poloxamer, and an optional viscosity-building agent, wherein the second individual reactive putty comprises an aqueous solution of a viscosity-building agent and, optionally, a particulate material, a colorant, and a therapeutic agent, and wherein the first and second reactive putties are intraoperatively mixed by hand-mixing or kneading to form the HPC.

In embodiments, the partially water miscible oxide is Pluronic L-35.

In embodiments, the optional viscosity-building agent is polyvinylpyrrolidone.

In embodiments, the aqueous solution of a viscosity-building agent comprises 70-85 (e.g., 70-80, 70-75, 75-80, or 80-85, for example, 70, 71, 72, 73, 74, 75, 76, 77, 78, 79, 80, 81, 82, 83, 84, or 85) wt % sodium carboxymethyl cellulose (based on the weight of the second putty).

In embodiments, the particulate material is tricalcium phosphate.

In embodiments, the colorant is gentian violet.

In embodiments, the therapeutic agent is a bone growth-promoting agent.

The disclosure also provides an HPC for use in any of the methods described herein, wherein the HPC comprises an ethylene glyocol-based system and is formed from mixing two individual reactive putties, wherein the first individual reactive putty comprises PEG monostearate, tetracalcium phosphate, phosphoserine, a buffer-producing agent admixed with a minimal amount of water or saline needed to produce a putty, wherein the second individual reactive putty comprises a mixture of PEG monostearate, PEG, an absorbable polyester or a nonabsorbable polyester, admixed with a minimal amount of water or saline needed to produce a putty, and wherein the first and second reactive putties are intraoperatively mixed by hand-mixing or kneading to form the HPC.

In any of the methods described herein, the HPC may comprise an ethylene glyocol-based system and is formed from mixing two individual reactive putties, wherein the first individual reactive putty comprises PEG monostearate, tetracalcium phosphate, phosphoserine, a buffer-producing agent admixed with a minimal amount of water or saline needed to produce a putty, wherein the second individual reactive putty comprises a mixture of PEG monostearate, PEG, an absorbable polyester or a nonabsorbable polyester, admixed with a minimal amount of water or saline needed to produce a putty, and wherein the first and second reactive putties are intraoperatively mixed by hand-mixing or kneading to form the HPC.

In embodiments, the absorbable polyester is polyglycolic acid.

In embodiments, the nonabsorbable polyester is polyethyleneterephthalate.

The disclosure also provides an HPC for use in any of the methods described herein, wherein the HPC comprises a polymethylmethacrylate system and is formed from mixing two individual reactive putties, wherein the first individual reactive putty comprises one or more liquid acrylate and methacrylate ester monomer(s), a viscosity builder and a free radical polymerization inhibitor, wherein the second individual reactive putty comprises a free radical source, an ionic radical source, and a viscosity builder, wherein the first and second individual reactive putties can be made putty-like by the addition of minimal quantities of an inert liquid diluent, and wherein the first and second reactive putties are intraoperatively mixed by hand-mixing or kneading to form the HPC.

In any of the methods described herein, the HPC can comprise a polymethylmethacrylate system and is formed from mixing two individual reactive putties, wherein the first individual reactive putty comprises one or more liquid acrylate and methacrylate ester monomer(s), a viscosity builder and a free radical polymerization inhibitor, wherein the second individual reactive putty comprises a free radical source, an ionic radical source, and a viscosity builder, wherein the first and second individual reactive putties can be made putty-like by the addition of minimal quantities of an inert liquid diluent, and wherein the first and second reactive putties are intraoperatively mixed by hand-mixing or kneading to form the HPC.

In embodiments, the viscosity builder is a polymethacrylate ester.

In embodiments, the free radical polymerization inhibitor is hydroquinone.

In embodiments, the free radical source is benzoyl peroxide.

In embodiments, the ionic radical source is ferric acetate.

In embodiments, the inert liquid diluent is N-methylpyrrolidone.

The disclosure also provides an HPC for use in any of the methods described herein, wherein the HPC comprises an epoxide system and is formed from mixing two individual reactive putties, wherein the first individual reactive putty comprises 60-80 wt % (e.g., 60-75, 60-70, 60-65, 65-80, 65-75, 65-70, 70-80, 70-75, 75-80, for example, 60, 61, 62, 63, 64, 65, 66, 67, 68, 69, 70, 71, 72, 73, 74, 75, 76, 77, 78, 79, or 80%) of triglycidal-p-amino phenol (based on the weight of the first putty) and 20-40 wt % (e.g., 20-35, 20-30, 20-25, 25-40, 25-35, 25-30, 30-40, 30-35, or 35-40, for example, 20, 21, 22, 23, 24, 25, 26, 27, 28, 29, 30, 31, 32, 33, 34, 35, 36, 37, 38, 39, or 40%) of a thickener (based on the weight of the first putty), wherein the second individual reactive putty comprises 60-80 wt % (e.g., 60-75, 60-70, 60-65, 65-80, 65-75, 65-70, 70-80, 70-75, 75-80, for example, 60, 61, 62, 63, 64, 65, 66, 67, 68, 69, 70, 71, 72, 73, 74, 75, 76, 77, 78, 79, or 80%) of dicyclohexyl amine (based on the weight of the second putty) and 20-40 wt (e.g., 20-35, 20-30, 20-25, 25-40, 25-35, 25-30, 30-40, 30-35, or 35-40, for example, 20, 21, 22, 23, 24, 25, 26, 27, 28, 29, 30, 31, 32, 33, 34, 35, 36, 37, 38, 39, or 40%) of a thickener (based on the weight of the second putty), and wherein the first and second reactive putties are intraoperatively mixed by hand-mixing or kneading to form the HPC.

In any of the methods described herein, the HPC may comprise an epoxide system and is formed from mixing two individual reactive putties, wherein the first individual reactive putty comprises 60-80 wt % (e.g., 60-75, 60-70, 60-65, 65-80, 65-75, 65-70, 70-80, 70-75, 75-80, for example, 60, 61, 62, 63, 64, 65, 66, 67, 68, 69, 70, 71, 72, 73, 74, 75, 76, 77, 78, 79, or 80%) of triglycidal-p-amino phenol (based on the weight of the first putty) and 20-40 wt % (i.e., 20, 21, 22, 23, 24, 25, 26, 27, 28, 29, 30, 31, 32, 33, 34, 35, 36, 37, 38, 39, or 40%) of a thickener (based on the weight of the first putty), wherein the second individual reactive putty comprises 60-80 wt % (i.e., 60, 61, 62, 63, 64, 65, 66, 67, 68, 69, 70, 71, 72, 73, 74, 75, 76, 77, 78, 79, or 80%) of dicyclohexyl amine (based on the weight of the second putty) and 20-40 wt (e.g., 20-35, 20-30, 20-25, 25-40, 25-35, 25-30, 30-40, 30-35, or 35-40, for example, 20, 21, 22, 23, 24, 25, 26, 27, 28, 29, 30, 31, 32, 33, 34, 35, 36, 37, 38, 39, or 40%) of a thickener (based on the weight of the second putty), and wherein the first and second reactive putties are intraoperatively mixed by hand-mixing or kneading to form the HPC.

In embodiments, the thickener in the first individual reactive putty is micronized polyvinyl pyrrolidone.

In embodiments, the thickener in the second individual reactive putty is micronized calcium phosphate.

In embodiments, the second individual reactive putty optionally additionally comprises 5 wt % tocopheryl acetate, 2 wt % antimicrobial agent, 10 wt % porogen, or any combination thereof.

In embodiments, the porogen comprises water soluble sugar fibers.

Also provided are custom implants formed from any of the HPCs disclosed herein.

In embodiments, the custom implant is in the form of a disc, plate, wrap, tape, cuff, pin, rod, barb, anchor, screw, spacer, facet dowel, shim, and/or interbody cage.

Any of the aspects and embodiments described herein can be combined with any other aspect or embodiment as disclosed here in the Summary of the Invention, in the Drawings, and/or in the Detailed Description of the Invention, including the below specific, non-limiting, examples/embodiments.

Unless otherwise defined, all technical and scientific terms used herein have the same meaning as commonly understood by one of ordinary skill in the art to which this application belongs. In the specification, the singular forms also include the plural unless the context clearly dictates otherwise.

Although methods and materials similar to or equivalent to those described herein can be used in the practice and testing of the application, suitable methods and materials are described below. All publications, patent applications, patents, and other references mentioned herein are incorporated by reference.

The references cited herein are not admitted to be prior art to the claimed application. In the case of conflict, the present specification, including definitions, will control. In addition, the materials, methods, and examples are illustrative only and not intended to be limiting.

Other features and advantages of the application will become apparent from the following detailed description in conjunction with the examples.

BRIEF DESCRIPTION OF THE FIGURES

FIG. 1A is a perspective view of fractured rib and long bones showing how the HPC may be applied between the fractured bones (110), packed into the hollow of the rib bone (120) like a dowel, as a ribbon or cuff wrapped around the circumference of the reduced fracture line (130), and pressed into adjacent drill holes across the fracture line (140), optionally connecting the holes with a portion of HPC shaped into a rod (140). FIG. 1B is a front view of a sternum showing the HPC applied to the edges of the cut sternum across its longitudinal length (150), across the reapproximated surface of the sternum like a plate or tape (160), and pressed into adjacent drill holes across the fracture line (170).

DETAILED DESCRIPTION OF THE INVENTION

Definitions

Figure 1A:
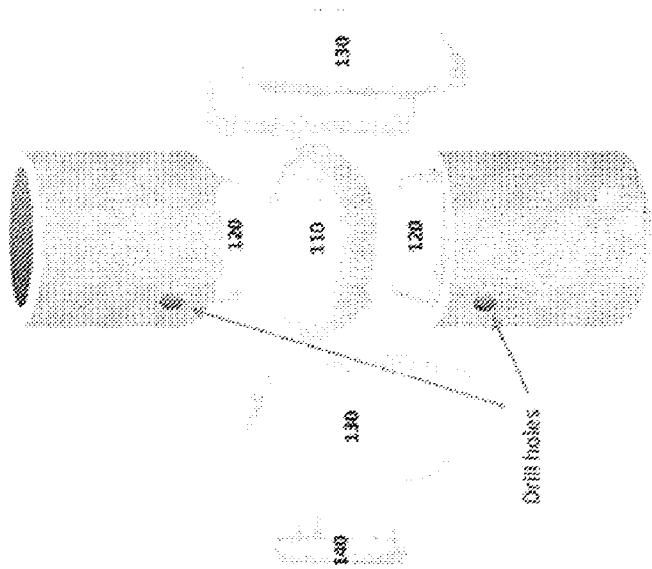
FIG. 1A-1B are schematics showing the re-approximation of adjacent bone fragments.
Figure 1A:
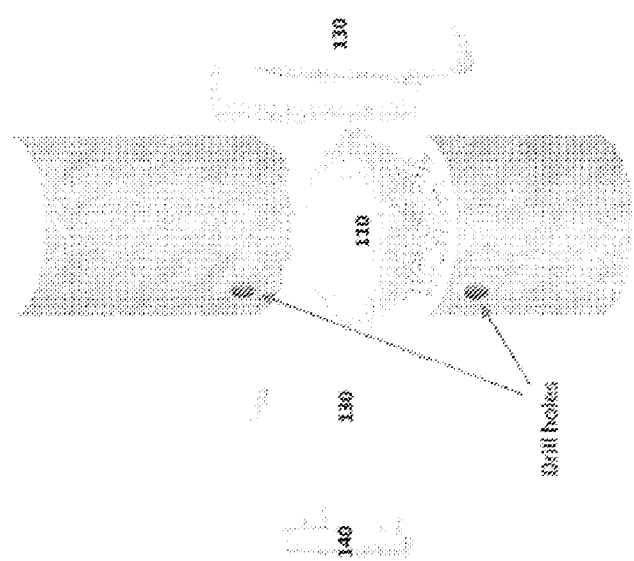

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

Unless specifically stated or obvious from context, as used herein, the terms "a," "an," and "the" are understood to be singular or plural.

Unless specifically stated or obvious from context, as used herein, the term "or" is understood to be inclusive.

As used herein, the term "about," unless indicated otherwise, refers to the recited value, e.g., amount, dose, temperature, time, percentage, etc., ±10%, ±9%, ±8%, ±7%, ±6%, ±5%, ±4%, ±3%, ±2%, or ±1%.

As used herein, the term "percent" (%), unless indicated otherwise, refers to percent by weight (e.g., wt % or % by weight).

As used herein, the terms "patient" or "subject" are used interchangeably herein to refer to any mammal, including humans, domestic and farm animals, and zoo, sports, and pet animals, such as dogs, horses, cats, and agricultural use animals including cattle, sheep, pigs, and goats. One preferred mammal is a human, including adults, children, and the elderly. A subject may also be a pet animal, including dogs, cats and horses. Preferred agricultural animals would be pigs, cattle and goats.

The phrases "therapeutically effective amount" and "effective amount" and the like, as used herein, indicate an amount necessary to administer to a patient, or to a cell, tissue, or organ of a patient, to achieve a therapeutic effect, such as an ameliorating or alternatively a curative effect. The effective amount is sufficient to elicit the biological or medical response of a cell, tissue, system, animal, or human that is being sought by a researcher, veterinarian, medical doctor, or clinician. Determination of the appropriate effective amount or therapeutically effective amount is within the routine level of skill in the art.

The terms "administering", "administer", "administration" and the like, as used herein, refer to any mode of transferring, delivering, introducing, or transporting a therapeutic agent to a subject in need of treatment with such an agent. Such modes include, but are not limited to, intraocular, oral, topical, intravenous, intraperitoneal, intramuscular, intradermal, intranasal, and subcutaneous administration.

As used herein, the term "substantially" means greater than 85% (e.g., greater than 85, 86, 87, 88, 89, 90, 91, 92, 93, 94, 95, 96, 97, 98, 99, or 100%).

As used herein, the terms "Pluronics" and "polaxmers" are used interchangeably herein to refer to nonionic triblock copolymers containing a central hydrophobic chain of polyoxypropylene flanked by two hydrophilic chains of polyoxyethylene The name of a given Pluronic starts with a letter to define its physical form at room temperature (L=liquid, P=paste, F=flake (solid)) followed by a two or three digit number. The first digit (or two digits in a three-digit number) multiplied by 300 indicates the approximate molecular weight of the hydrophobe, and the last digit multiplied by 10 gives the percentage polyoxyethylene content.

The terms "degradable", "biodegradable", "resorbable", and "absorbable" and the like are used interchangeably herein to refer to the ability of the claimed compositions to degrade (partially or completely) under physiological conditions into non-toxic products that can be metabolized or excreted from the body within a period of time, generally several days and up to a year or about 18 to 24 months (e.g., 18, 19, 20, 21, 22, 23, or 24 months) or longer. In one embodiment, the composition is fully biodegradable within about 12 months. Compositions may be considered non-biodegradable if they remain stable in vivo for periods exceeding about ten years.

The terms "set" and "cure" are used interchangeably herein and refer to the transition from a semi-solid, spreadable, extrudable (e.g., from a syringe or similar device), hand-moldable, and formable material into a material that is hardened and resists compressive or tensile deformation.

The term "biocompatible" refers to materials that do not induce undesirable effects when administered or implanted in vivo, for example, an immune reaction and/or an inflammatory reaction, or other adverse reaction that is detrimental to wound healing and/or to the implant recipient. A biocompatible material may also be referred to as "nontoxic".

The term "putty" as used herein refers to a composition that is soft enough to be spreadable or extrudable, e.g., having a stiffness in the range of 4-6 millimeters (e.g., 4, 5, or 6 millimeters), and also refers to a somewhat stiffer composition that is still soft enough to be hand-moldable, e.g., having a stiffness in the range of 1-1.5 millimeters (e.g., 1, 1.1, 1.2, 1.3, 1.4, or 1.5 millimeters), as measured by a penetrometer at room temperature exerting a force of 50 grams for 5 seconds.

As used herein, the term "intraoperatively" indicates that there is a short period of time between the mixing of the individual reactive putties in order form the single homogeneous putty composition ("HPC") and the application of the HPC to bone and/or cartilage. For example, the period of time may be less than 20 minutes (e.g., less than 19, 18, 17, 16, 15, 14, 13, 12, 11, 10, 9, 8, 7, 6, 5, 4, 3, 2, 1 minutes).

The disclosure provides solid settable surgical compositions generally in the form of an adhesive putty composition which may be formed from any of polyisocyanates, cyanoacrylate and methylidene malonate esters, magnesium phosphates, polyethylene glycols, poly (methyl methacrylate), and/or epoxides, and methods of using same in surgical procedures which take advantage of the unique properties of these solid adhesive settable materials.

In embodiments, the compositions described here are generally formed from the combination of two or more separate, individual reactive putty materials, referred to herein as "multi-putty compositions" which when mixed into a single HPC react with each other to initiate a chemical reaction which transforms the HPC from an initially soft, formable, adhesive, and generally hand-moldable putty material into a hardened cement-like material that resists mechanical deformation. The HPC is never in a liquid form. Generally, the individual putties used to form the HPC are adapted to be mixed together in a 1:1 ratio, but in some embodiments the putties may be mixed in a ratio of from 1:1 to 1:0.5 (e.g., 1:1, 1:0.9, 1:0.8; 1:0.7; 1:0.6; or 1:0.5).

The HPC formed from mixing the multi-putty compositions, and, in some cases, from a single putty composition, as described in more detail infra, has unique properties of elasticity, stiffness, and cohesiveness that make it useful as a multifunctional surgical implant material. For example, the HPC can provide mechanical hemostasis when applied to bleeding bone; fixation of a restored alignment or reapproximation; stabilization of a repaired fracture; a filler, spacer, or cushion for void or space in bone or cartilage; stabilization of surgical hardware; and/or improved bone healing at the implant site. Healing is improved, for example, due to the porous structure of the HPC material and/or through the incorporation of optional osteogenic and osteoconductive agents into the HPC. In addition, for the degradable and partially degradable embodiments, healing is improved through the eventual replacement of the HPC material by new bone.

The HPC can generally be used both for fixation and stabilization because, in its initial form, the HPC material is very adhesive, adhering even to the surface of bleeding bone, thereby making it highly suitable for fixation, while within minutes it cures into a hardened cement-like form that provides stabilization of the fracture line. In this context, "fixation" refers to the process of joining and holding two bone fragments together, for example, in the context of reapproximation of adjacent cut or fractured bone. In addition, as the HPC material cures, it becomes less adhesive and may be used in this form (or in its adhesive form) as a filler material to occupy a void or space in bone, or in cartilage, for example to provide a cushion or spacer between adjacent pieces of bone or cartilage.

Its unique physical properties of elasticity, stiffness, and cohesiveness also enable the HPC to be formed into various shapes and used, for example, as a custom implant, as well as to perform a number of functions typically performed by conventional surgical hardware, including for example, the fixation and/or stabilization function performed by a surgical such as plates, dowels, bridges, rods, scaffolds, pins, screws, tines, etc. The advantageous physical properties of the HPC allow it to be formed into suitable shapes to replace or reduce the use of such conventional surgical hardware. For example, the HPC may be formed into a spacer, cage, wrap, tape, cuff, shim, plate, dowel, bridge, rod, scaffold, pin, screw, tine, etc., as described in more detail infra.

The HPC is also a highly versatile surgical material. For example, it may serve as a tissue adhesive and cement, as well as an internal orthopedic cast.

In general, use of the HPC as described here provides for improved surgical methods which are more efficient both in terms of overall costs, because of the reduction or elimination of conventional hardware, and in terms of the time needed to complete the surgical procedure. As discussed in more detail below, representative examples of surgical methods utilizing the HPC included methods for re-approximation of cut or fractured bone, including long bones, short bones, cranial bones, bones of the hands and feet, as well as the sternum, and for spinal fusion, hip, and knee surgery.
Polyisocyanate-Based Compositions In embodiments, the multi-putty compositions react when mixed to form a polyurethane polymer or polyurethane urea polymer. The HPC remains easily spreadable, hand-moldable, and/or extrudable (e.g., from a syringe or similar device) for several minutes after its formation, and gradually transitions into a stiffer form that remains hand-moldable and formable for a period of time. In embodiments, the period of time is at least about 5-10 minutes (e.g., 5, 6, 7, 8, 9, or 10 minutes), after which time it hardens into a form that resists mechanical deformation within about 20 minutes. In a "fast-setting" embodiment, the period of time to remain hand-moldable and formable is at least about 30 seconds to two minutes (e.g., 30 seconds, 45 seconds, 60 seconds, 75 seconds, 90 seconds, 105 seconds, or 120 seconds), after which time it hardens into a form that resists mechanical deformation within about 5-10 minutes (e.g., 5, 6, 7, 8, 9, or 10 minutes). In the present context, the hardened form is suitable for mechanical drilling or tapping without cracking or breaking, but the HPC may not be fully set, that is, the polymer forming reaction will not have gone to completion.

The HPC formed from mixing the multi-putty compositions described here has unique properties of elasticity, stiffness, and cohesiveness paired with sufficient adhesive strength to allow it to adhere firmly to the wet surface of living tissue, especially bone, even in the presence of active bleeding and/or surgical irrigation. This renders the HPC surprisingly versatile in the surgical theater. As described in more detail below, these properties allow the individual reactive putties to be quickly and easily mixed during surgery, either by hand or via a suitable device, to form the HPC. The HPC may then be intraoperatively sized, shaped, and applied to the surgical site, again either by hand with or without the aid of common surgical tools, or using a suitable device, such as a 3D printer. The HPC can be formed within minutes into any of a range of shapes to fit the surgical site and the needs of the surgeon. For example, and as described in more detail below, the HPC may be formed into the shape of a disc, plate, wrap, tape, cuff, pin, rod, barb, anchor, screw, or tine, e.g., for use in re-approximation of cut or fractured bone. In addition, the HPC may also be formed into the shape of a spacer, facet dowel, or interbody cage, e.g., for use in spinal surgery. The HPC may also be formed into an acetabulum cup or pressed into place as a cup liner, e.g., for use in hip surgery. Accordingly, the disclosure provides methods for using the HPC in surgical procedures that take advantage of its unique properties.

In embodiments, the compositions described here consist of two or more separate, individual reactive putty materials which when mixed together react to form the HPC which cures over a period of time in situ into a polyurethane urea polymer. Polyurethane urea polymer formation takes place, generally, as water present at the surgical site reacts with isocyanate groups in the HPC, even if there is no polyamine component to the separate reactive putties. Reaction of available isocyanate groups with water in situ generates unstable carbamic acid which rapidly decomposes into gaseous carbon dioxide and the corresponding amine. The amine readily reacts with proximal unreacted isocyanate to form a urea linkage, thereby forming the polyurethane urea polymer. As the carbon dioxide bubbles through the HPC, it forms pores which allow the ingress of additional water and bodily fluids as well as cells (e.g., osteoclasts, blood cells) into the composition in situ. The final cured composition is thus sufficiently porous to promote tissue repair and remodeling. In embodiments, porosity can be controlled, for example, by modulating the rate of ingress of water into the setting composition. This can be achieved by modulating the viscosity of the composition (high viscosities will slow the ingress of water) or by addition of a hydrophobic additive to the composition. If desired, additional pore-forming components may be added to increase porosity, for example through the inclusion of a porous material, or through the inclusion of a small amount of water, or through the inclusion of one or more surfactants, such as a poloxamer (e.g., Synperonics®, Pluronics®, and Kolliphor®) or a polysorbate-type nonionic surfactant formed by the ethoxylation of sorbitan before the addition of lauric acid (e.g., Tween® 20, Tween® 80), and/or by including a cell opener as optional additives. In embodiments, the porous material may be a carboxymethyl cellulose (e.g., sodium carboxymethyl cellulose), an oligomer of ethylene oxide (e.g., polyethylene glycol, polyoxyethylene, or polyethylene oxide), or similar material that absorbs water. Generally, such additional pore-forming components are included in amounts of from 5-50 wt % (e.g., 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45, or 4-50, for example, 5, 10, 15, 20, 25, 30, 35, 40, 45, or 50 wt %).

In embodiments, the HPC has an average pore size in the range of from about 5 to 700 microns. In embodiments, the average pore size is from about 5 to 100 microns, from about 5 to 300 microns, from about 5 to 500 microns, and from about 5 to 700 microns. In embodiments, the average pore size is from about 100 to 300 microns, from about 200 to 500 microns, from about 300 to 600 microns, and from about 500 to 700 microns, or greater. The porosity of the HPC composition may range from about 2-70% (e.g., 2-65, 2-60, 2-55, 2-50, 2-45, 2-40, 2-35, 2-30, 2-25, 2-20, 2-15, 2-10, 2-5, 5-70, 5-65, 5-60, 5-55, 5-50, 5-45, 5-40, 5-35, 5-30, 5-25, 5-20, 5-15, 5-10, 10-70, 10-65, 10-60, 10-55, 10-50, 10-45, 10-40, 10-35, 10-30, 10-25, 10-20, 10-15, 15-70, 15-65, 15-60, 15-55, 15-50, 15-45, 15-40, 15-35, 15-30, 15-25, 15-20, 20-70, 20-65, 20-60, 20-55, 20-50, 20-45, 20-40, 20-35, 20-30, 20-25, 15-70, 25-65, 25-60, 25-55, 25-50, 25-45, 25-40, 25-35, 25-30, 30-70, 30-65, 30-60, 30-55, 30-50, 30-45, 30-40, 30-35, 35-70, 35-65, 35-60, 35-55, 35-50, 35-45, 35-40, 40-70, 40-65, 40-60, 40-55, 40-50, 40-45, 45-70, 45-65, 45-60, 45-55, 45-50, 50-70, 50-65, 50-60, 50-55, 55-70, 55-65, 55-60, 60-70, 60-65, or 65-70, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70%) by volume.

In embodiments, a suitable amount of a primary or secondary amine can be introduced, either into a reactive putty or to the HPC itself, instead of water, to react with the isocyanate and form a polyurethane urea polymer.

Generally, the HPC cures into a hardened composition in the range of room temperature to body temperature, over a period of time ranging from about 20 minutes to 3 hours (e.g., 20, 30, 40, 50, 60, 70, 80, 90, 100, 110, 120, 130, 140, 150, 16, 170, or 180 minutes), or in a fast-setting embodiment, from about 5-10 minutes (e.g., 5, 6, 7, 8, 9, or 10 minutes), without the need to apply external heat in excess of the ambient heat of the room (about 24-26° C.) or the heat of the human body (about 37° C.). The fully cured HPC has mechanical properties suitable for drilling or accepting a surgical screw without shattering or splintering. For example, in embodiments, the fully cured HPC is drillable or machinable and has a compressive strength in the range of 30-150 MPa (e.g., 30, 35, 40, 45, 50, 55, 60, 65, 70, 75, 80, 85, 90, 95, 100, 105, 110, 115, 120, 125, 130, 135, 140, 145, or 150 MPa) or 30-50 MPa (e.g., 30, 35, 40, 45, or 50 MPa) and a tensile strength in the range of 20-80 MPa (e.g., 20, 25, 30, 35, 40, 45, 50, 55, 60, 65, 70, 75, or 80 MPa) or 20-40 MPa (e.g., 20, 25, 30, 35, or 40 MPa). In embodiments, the fully cured HPC also has an elasticity defined by a Modulus of Elasticity of from 1,400-1,800 MPa (e.g., 1400, 1450, 1500, 1550, 1600, 1650, 1700, 1750, or 1800 MPa) or 1,400-1,500 MPa (e.g., 1400, 1450, or 1500 MPa). Thus, in embodiments, the HPC, when fully cured, has a compressive strength, tensile strength, and elasticity suitable for use in bone repair or reconstruction.

In accordance with the compositions and methods described here, the polymer forming reaction goes to completion without generating tissue-damaging amounts of heat. For example, the maximum exotherm (amount of heat i.e., temperature increase) generated by a polyurethane urea polymer forming reaction does not raise the temperature of the HPC more than to about 40° C. and generally less, for example around 37° C. The exotherm is a measure of the amount of heat liberated by a chemical reaction. For example, if the reaction liberates 10 units of heat, it has an exotherm of 10 and will raise the temperature of the reacting mass by 10° C. In general, the exotherm of the reaction may be kept low in part through the use of prepolymers in the separate, individual reactive putty materials.

In embodiments, one individual reactive putty used to form the HPC will comprise an isocyanate component and one will comprise a polyol and/or polyamine component. Each reactive putty may additionally comprise an optional particulate component. The separate isocyanate putty and the separate polyol/polyamine putty are preferably in the form containing a prepolymer with an excess reactive component, i.e., excess isocyanate, polyol, or polyamine, depending on whether each prepolymer is isocyanate-terminated, hydroxyl-terminated, or amine-terminated. Accordingly, the terms "isocyanate component", and "polyol/polyamine component" may refer to a prepolymer of the isocyanate or the polyol/amine. In other words, the isocyanate and polyol/polyamine components are in the form of prepolymers with optional free isocyanate or optional free polyol/polyamine. The prepolymer may consist, for example, of a reactive isocyanate-terminated prepolymer formed from one or more polyols reacted with excess isocyanate; or the prepolymer may consist of a reactive hydroxyl-terminated prepolymer formed from one or more isocyanates reacted with excess polyol; or the prepolymer may consist of a reactive amine-terminated prepolymer formed from one or more isocyanates reacted with excess polyamine. The individual reactive putties will each contain a different prepolymer, e.g., an isocyanate-terminated prepolymer or a hydroxyl- or amine-terminated prepolymer, along with excess isocyanate or excess polyol/polyamine, respectively.

In embodiments, the amount of prepolymer is sufficient to allow for about 40-60% (i.e., 40, 41, 42, 43, 44, 45, 46, 47, 48, 49, 50, 51, 52, 53, 54, 55, 56, 57, 58, 59, or 60%) of the polymer forming reaction remaining at the time of mixing to form the HPC. The result is a composition that generates less heat as it sets in situ. In addition, because of the viscous nature of the HPC, the reaction proceeds more slowly than it would, for example, in a liquid medium, thereby generating less heat per unit time than the same composition using liquid components. In addition, and as described in more detail below, the choice of the particulate material in the individual putties may further help to limit the exotherm, for example by choosing a material with relatively good heat dissipation. An example is ceramic materials, such as calcium phosphate, that dissipate heat more readily than other materials.

The fully cured HPC is biocompatible and fully or partially biodegradable and/or bioabsorbable under physiological conditions. The HPC is also fully or partially biodegradable and/or bioabsorbable under physiological conditions.

In embodiments, the HPC is fully or partially degradable under physiological conditions within a period of time. Where the HPC is fully degradable, it is degraded within about 3-6 months (e.g., 3, 4, 5, or 6 months) or within about 6-12 months (e.g., 6, 7, 8, 9, 10, 11, or 12 months). In embodiments, the HPC is formed from a combination of fully degradable, partially degradable, and/or non-degradable components. For example, the isocyanate component and/or the polyol/polyamine component of the individual reactive putties may be fully or partially biodegradable while the particulate component may be fully or partially absorbable, or non-absorbable. In embodiments, the HPC may be considered "partially degradable" because it includes some materials that do not degrade and are not absorbed.

In embodiments, the individual putties used to form the HPC may contain one or more additive materials which function to promote the growth of new bone, including, for example one or more of a bone-derived material such as a bone autograft material, a partially or fully demineralized bone matrix ("DBM") material, or a DBM derivative material. The individual putties may also contain one or more additives for the management of pain at the surgical site, for example an analgesic, and to lower the risk of infection, such as an antibiotic or antimicrobial substance. The optional additives that may be included are described in more detail below.

As discussed above, the HPC is formed from the mixing of two or more separate, individual reactive putty materials. In embodiments, the individual reactive putties described here are characterized as having a stiffness as measured by a penetrometer of about 5.2 millimeters and within a range of about 4-6 millimeters (e.g., 4, 5, or 6 millimeters). The penetrometer test measures stiffness of a material by measuring the depth of penetration of a rod, cone or needle driven into the material by a known force, e.g., about 50 grams in the present case, for a period of time, e.g., about 5 seconds. Upon mixing the individual reactive putties at room temperature to form the HPC, the HPC retains a similar stiffness in the range of about 4-6 millimeters (e.g., 4, 5, or 6 millimeters) for at least about 2 minutes, and then gradually hardens as it cures. For example, after about 5 minutes, the stiffness of the HPC is about 1.3 millimeters and within a range of about 1-1.5 millimeters (e.g., 1, 1.1, 1.2, 1.3, 1.4, or 1.5 millimeters). By 15 minutes, the stiffness has been reduced to about 0.3 millimeters and within a range of from 0.2-0.4 millimeters (e.g., 0.2, 0.3, or 0.4 millimeters). The HPC is fully hardened within about 20 minutes, whereupon the stiffness is about 0.1 millimeter. In embodiments, the HPC is machine drillable within about 5-20 minutes (e.g., 5, 6, 7, 8, 9. 10, 11, 12, 13, 14, 15, 16, 17, 18, 19, or 20 minutes), and thereafter.

The individual reactive putty component used to form the HPC is generally described here using a two-putty system. However, the skilled person can easily envision a multi-putty system based on same. For example, in embodiments a multi-putty system may consist of an isocyanate putty, a polyol putty or polyamine putty, and an additive putty that may contain further reactive components, such as a polyamine or polyol, and/or non-reactive components, such as a particulate material, e.g., a ceramic material or other particulate material as described herein.

In some embodiments the particulate component is optional, and the individual reactive putties comprise only an isocyanate component, a polyol component, and an optional polyamine. In accordance with these "non-particulate" embodiments, the isocyanate and polyol components are in the form of prepolymers and optional free isocyanate or polyol. In embodiments, the prepolymer component of one reactive putty consists of a reactive isocyanate-terminated prepolymer formed from one or more polyols reacted with excess isocyanate and the prepolymer component of the other reactive putty consists of a reactive hydroxyl-terminated prepolymer formed from one or more isocyanates reacted with excess polyol. Generally, in "non-particulate" embodiments, the prepolymers will form about 5-100 wt % of each individual reactive putty. In embodiments, the prepolymers will form about 5-50 wt % of each individual reactive putty. In embodiments, the prepolymers will form about 15-50 wt % or about 20-50 wt % of each individual reactive putty where there is no particulate component.

As noted above, generally each individual reactive putty used to form the HPC comprises an isocyanate component and/or a polyol component, a particulate component, and/or an optional polyamine. In embodiments, a portion of the isocyanate component and the polyol and/or polyamine component is present in the form of a prepolymer. A polyurethane-forming prepolymer is a polymer having reactive end groups, e.g., isocyanate, hydroxyl, or amino groups. Generally, the amount of prepolymer in each individual reactive putty will be similar, but need not be the same. In embodiments, the prepolymer forms from 2-10 wt % (e.g., 2, 3, 4, 5, 6, 7, 8, 9, or 10 wt %) of an individual reactive putty. In embodiments, the prepolymer forms from about 2-5 wt % (e.g., 2, 3, 4, or 5 wt %), about 5-7 wt % (e.g., 5, 6, or 7 wt %), or about 3-8 wt % (e.g., 3, 4, 5, 6, 7, or 8 wt %) of an individual reactive putty. In accordance with embodiments comprising prepolymer, each prepolymer containing putty will also contain excess unreacted isocyanate (where the prepolymer is an isocyanate-terminated prepolymer) or excess unreacted polyol or polyamine (where the prepolymer is a hydroxyl- or amino-terminated prepolymer). In embodiments, the amount of excess isocyanate may be in the range of from 20-40 wt % (e.g., 20, 21, 22, 23, 24, 25, 26, 27, 28, 29, 30, 31, 32, 33, 34, 35, 36, 37, 38, 39, or 40 wt %), or from 25-35 wt % (e.g., 25, 26, 27, 28, 29, 30, 31, 32, 33, 34, or 35 wt %), or from 30-45 wt % (e.g., 30, 31, 32, 33, 34, 35, 36, 37, 38, 39, 40, 41, 42, 43, 44, or 45 wt %), of an individual reactive putty. In accordance with this embodiment, the counterpart putty may contain from 1-5 wt % (e.g., 1, 2, 3, 4, or 5 wt %), or from 1-4 wt % (e.g., 1, 2, 3, or 4 wt %), or from 1-3 wt % (e.g., 1, 2, or 3 wt %) of excess polyol or polyamine.

In embodiments, each individual reactive putty comprises a prepolymer such that, for a pair of putties, one putty comprises a prepolymer component that is a reactive isocyanate-terminated prepolymer formed from one or more polyols and/or polyamines reacted with excess isocyanate; and the second putty comprises a prepolymer component that is a reactive hydroxyl- and/or amino-terminated prepolymer formed from one or more isocyanates reacted with excess polyol and/or polyamine. Thus, the individual reactive putties will each contain a different prepolymer component, e.g., an isocyanate-terminated prepolymer or a hydroxyl- and/or amino-terminated prepolymer, along with excess isocyanate and/or excess polyol or polyamine, respectively, in amounts sufficient to complete the polyurethane urea forming reaction upon mixing the individual reactive putties together to form the HPC, as described above.

One or more of the individual reactive putties may further comprise one or more optional additives. In embodiments, the optional additive is selected from a reactive additive, such as a chain extender, e.g., 1,4-butanediol, hexanediol, cyclohexane dimethanol, and hydroquinone bis (2-hydroxyethyl) ether (HQEE), and a non-reactive additive, such as esters of glycerin, e.g., as glyceryl tripropionate or glyceryl triacetate (triacetin), a divalent metal salt of a fatty acid (e.g., calcium, magnesium, or zinc stearate), and tocopherol esters such as tocopheryl acetate (Vitamin E acetate) 3-7% (e.g., 3, 4, 5, 6, or 7%), and combinations of any or all of the foregoing reactive and non-reactive additives. In embodiments, one or more of the individual reactive putties contains one or more additives selected from reactive 1,4-butanediol and non-reactive triacetin, calcium stearate, and tocopheryl acetate. In embodiments, the one or more optional additives may further comprise one or more of an alkylpyrrolidone, a polyamine such as chitosan or alpha-polylysine, triethanolamine, a colorant, an antioxidant, and a therapeutic agent. In embodiments, the alkylpyrrolidone is N-methyl-2-pyrrolidone (NMP). In embodiments, the polyamine is included to increase the rate of hardening of the HPC, e.g., to form the "fast-setting" embodiment. In embodiments, the therapeutic agent is selected from an anticancer agent, an anti-inflammatory agent, an antimicrobial agent, an anesthetic agent, an analgesic agent, an osteogenic agent, and combinations thereof. In embodiments, the amount of alkylpyrrolidone in the composition is in the range of from about 0.1-10 wt % (e.g., 0.1-0.5, 0.1-1, 0.1-5, 0.5-1, 0.5-5, 0.5-10, 1-5, 1-10, 5-10, for example, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 wt %).

In embodiments, the reactivity of chitosan can be adjusted by varying the degree of deacetylization which varies the number of amino groups available to react with the isocyanate, or by forming the partial ammonium salt of deacetylated chitosan. Accordingly, in embodiments, the chitosan is deacetylated chitin or chitosan, or a salt thereof, such as an ammonium salt. In embodiments, the amount of chitosan in the composition is in the range of from about 0.1-10 wt % (e.g., 0.1-0.5, 0.1-1, 0.1-5, 0.5-1, 0.5-5, 0.5-10, 1-5, 1-10, 5-10, for example, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 wt %. In embodiments, an aminoglycoside such as gentamicin, tobramycin, or streptomycin, etc. can be used to replace the amino groups of chitosan.

Other optional additives are described infra.

In accordance with any of the foregoing embodiments, the amount of particulate material incorporated into each individual reactive putty will be an amount sufficient to provide the desired stiffness. For example, each individual putty may independently comprise particulate material in an amount ranging from about 50-90 wt % (e.g., 50, 51, 5,2, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %), or from about 50-80 wt % (e.g., 50, 51, 5,2, 53, 54, 55, 56, 57, 58, 59, 60, 61, 62, 63, 64, 65, 66, 67, 68, 69, 70, 71, 72, 73, 74, 75, 76, 77, 78, 79, or 80 wt %), or from about 50-60 wt % (e.g., 50, 51, 5,2, 53, 54, 55, 56, 57, 58, 59, or 60 wt %), or from about 70-80 wt % (e.g., 70, 71, 72, 73, 74, 75, 76, 77, 78, 79, or 80 wt %), based on the weight of the individual putty. The total amount of particulate material in the HPC will be in the range of from about 60-75 wt (e.g., 60-70, 60-65, 65-75, 65-70, 60-75, for example, 60, 61, 62, 63, 64, 65, 66, 67, 68, 69, 70, 71, 72, 73, 74, or 75 wt %). For less viscous putties that when mixed form an HPC that is more easily spreadable, less particulate material may be used. For example, each individual putty may independently comprise particulate material in an amount ranging from about 10-50 wt % (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt %), or about 10-40 wt % (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 wt %) in the individual putties, to give a total amount of particulate material in the HPC of from about 45-55 wt % (e.g, 45, 46, 47, 48, 49, 50, 51, 52, 53, 54, or 55 wt %).

The Isocyanate Component

The term "isocyanate" is used generically to refer to diisocyanates, and polyisocyanates. In embodiments, the isocyanate component comprises or consists of an aromatic isocyanate, an aliphatic isocyanate, a cycloaliphatic isocyanate, or an adduct of an isocyanate, or a mixture of any of the foregoing. A mixture refers to a mixture of two or more of the foregoing. For example, the isocyanate component may comprise or consist of a mixture of two or more isocyanates independently selected from an aromatic isocyanate, an aliphatic isocyanate, a cycloaliphatic isocyanate, and an adduct of an isocyanate. In addition, the isocyanate component may comprise or consist of a mixture of two or more aromatic isocyanates, two or more aliphatic isocyanates, two or more cycloaliphatic isocyanates, etc.

In embodiments, the isocyanate is an aliphatic isocyanate selected from the group consisting of ethyl lysine diisocyanate, hexamethylene diisocyanate, cyclohexyl diisocyanate, or a mixture of any two or more of the foregoing.

In embodiments, the adduct of an isocyanate is selected from a hexamethylene diisocyanate trimer (DESMODUR N-3390) and a hexamethylene diisocyanate biuret (DESMODUR N-100) both commercially available from Bayer AG.

In embodiments, the isocyanate component comprises a polyaromatic di- or polyisocyanate having at least one hydrolysable linkage bridging at least two of the aromatic rings. In certain embodiments, the hydrolysable linkage bridging the aromatic rings is derived from glycolic acid, lactic acid, caprolactone, or p-dioxanone. In most cases, the hydrolyzable linkage is an ester which may degrade into an acid and an alcohol as a result of exposure to water or to naturally occurring esterases. Amide linkages are usually more difficult to hydrolyze than esters. Another option is the easily hydrolyzable acid anhydride linkage. Sulfonamides may also be considered in this context.

In embodiments, the isocyanate component comprises or consists of a resorbable lactyl diisocyanate, preferably benzoic acid, 4-isocyanato-1,1'-[oxybis[2,1-ethanediyloxy(1-methyl-2-oxo-2,1-ethanediyl)]]ester, referred to herein as ALD.

The Polyol/Polyamine Component

The polyol/polyamine component may comprise any number of suitable diols, polyols, and polyamines, including, but not limited to, biocompatible, naturally occurring polyols or polyamines, synthetic polyols or polyamines, and mixtures thereof. The polyol/polyamine component may comprise degradable or non-degradable materials, or a mixture of the two. The term "polyol" in the context of the "polyol/polyamine component" refers to both diols and polyols. Thus, the polyol or polyamine component may comprise or consist of one or more different diols, diamines, polyols, polyamines, or mixtures of two or more diols, diamines, polyols and/or polyamines.

Suitable polyols include diols and polyols having repeating units containing up to about 18 carbon atoms. Examples of suitable diols include, but are not limited to, 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,8-octanediol and combinations thereof. Examples of preferred polydiols include polyethylene glycol with molecular weights of from about 500 to about 10000, polytetramethylene ether glycols, polyols derived from glycolide, lactide, trimethylenecarbonate, p-dioxanone and/or caprolactone with molecular weights of about 500 to about 10000 (i.e., 500, 1000, 1500, 2000, 2500, 3000, 3500, 4000, 4500, 5000, 5500, 6000, 6500, 7000, 7500, 8000, 8500, 9000, 9500, or 10000 or 500-1000, 500-5000, 1000-5000, 1000-10000, or 5000-10000).

In embodiments, the polyol is a synthetic polyol selected from a polycaprolactone polyol, polyester polyols, polyadipate polyols (e.g., poly(hexane-adipate) diol, poly(butane-adipate) diol, poly(ethylene/propylene-adipate) diol, poly(hexane/adipate/isophthalate diol), and polyols that have been derived from a synthetic acid (e.g., isophthalic acid, maleic acid). An example of a suitable biocompatible synthetic polyol is a polycaprolactone diol that is commercially available from Dow Chemical under the trade name TONE 32 B8. Further non-limiting examples of suitable synthetic polyols include poly(oxypropylene) glycols, poly(oxytetramethylene) glycols, and poly(oxyethylene) glycols. In one embodiment, the synthetic polyol is selected from a poloxamer (e.g., a Pluronic™) polycaprolactone co-glycolide or a polycaprolactone co-lactide.

In embodiments, the polyol is a naturally occurring polyol selected from castor oil and lesquerella oil, the polyols that may be obtained by chemical modification of naturally occurring vegetable oils (e.g., castor oil, olive oil, sesame oil, corn oil), naturally occurring oils that have been transesterified (e.g., a modified castor oil polyol that has been prepared by the transesterification reaction of natural castor oil with suitable crosslinkers (e.g., glycerol, trimethylolpropane, and the like) or with acids (such as adipic acid), and naturally occurring oils that have been hydrogenated. Further non-limiting examples of suitable naturally occurring polyols include the commercially available castor-oil-based polyols CASPOL™5001, CASPOL™1962, and CASPOL™5004 (all available from CasChem, Inc.). In certain embodiments, the polyol is not a naturally occurring polyol such as castor oil and lesquerella oil.

The polyamine may be a primary or secondary diamine, or a hindered amine. Non-limiting examples of suitable polyamines include, hindered diamine (e.g., isophorone diamine, "IPDA"), 1,4-cyclohexyl diamine, 1,3-pentane diamine, and aliphatic secondary diamines, and mixtures thereof. In certain embodiments, aliphatic diamines and cycloaliphatic diamines may be particularly suitable, and may offer improved biocompatibility. Commercially available examples of suitable polyamines include CLEARLINK 1000 (Dorf Ketal).

Amines including diamines that may be suitable for use include but are not limited to polyethyleneimines, PEG amines with weight average molecular weights from about 500 to about 5,000 (e.g 500, 1000, 1500, 2000, 2500, 3000, 3500, 4000, 4500, or 5000 or 500-1000, 500-5000, or 1000-5000), polyoxypropylenediamines available under the tradename JEFFAMINES (Huntsman Corporation, Houston, Tex.) and polyetherdiamines in general, spermine, spermidine, hexamethylenediamine, octamethylenediamine, decamethylenediamine, dodecamethylenediamine, hexadecamethylenediamine, octadecamethylenediamine, polyamidoamine dendrimers, PEG-dextran conjugates, cysteines, proteins and peptides containing amines, non-biologically active symmetrical and asymmetrical diamino compounds containing saturated and unsaturated, substituted and unsubstituted alkyl, aryl and alkylaryl groups having from about 2 to about 18 carbon atoms (i.e., 2, 3, 4, 5, 6, 7, 8, 9, 10, 11, 12, 13, 14, 15, 16, 17, or 18 carbon atoms), e.g., from about 2-4, 2-5, 2-6, 2-7, 2-8, 2-9, 2-10, 2-11, 2-12, 2-13, 2-14, 2-15, 2-16, 2-17, 2-18, 3-5, 3-6, 3-7, 3-8, 3-9, 3-10, 3-11, 3-12, 3-13, 3-14, 3-15, 3-16, 3-17, 3-18, 4-6, 4-7, 4-8, 4-9, 4-10, 4-11, 4-12, 4-13, 4-14, 4-15, 4-16, 4-17, 4-18, 5-7, 5-8, 5-9, 5-10, 5-11, 5-12, 5-13, 5-14, 5-15, 5-16, 5-17, 5-18, 6-8, 6-9, 6-10, 6-11, 6-12, 6-13, 6-14, 6-15, 6-16, 6-17, 6- 18, 7-9, 7-10, 7-11, 7-12, 7-13, 7-14, 7-15, 7-16, 7-17, 7-18, 8-10, 8-11, 8-12, 8-13, 8-14, 8-15, 8- 16, 8-17, 8-18, 9-11, 9-12, 9-13, 9-14, 9-15, 9-16, 8-17, 9-18, 10-12, 10-13, 10-14, 10-15, 10-16, 10-17, 10-18, 11-13, 11-14, 11-15, 11-16, 11-17, 11-18, 12-14, 12-15, 12-16, 12-17, 12-18, 13-15, 13-16, 13-17, 13-18, 14-16, 14-17, 14-18, 15-17, 15-18, or 16-18 carbon atoms. Further, the diamino compound can be synthesized containing a hydrolyzable link such as one or more ester groups to accelerate the rate of polymer degradation (absorption) in the body.

In embodiments, the polyol component comprises one or more polyols selected from butanediol, polytetramethylene ether glycol, tris-hydroxymethyl propane, monosubstituted tris-hydroxymethyl propane, pentaerythritol, monosubstituted pentaerythritol, hydrogenated dihydroxypolyisoprene, hydroxyl terminated polybutadiene, hydroxyl terminated homopolymers or copolymers of ethyelene oxide and propylene oxide, hydroxyl terminated homopolymers or copolymers of glycolide, lactide, p-dioxanone, trimethylene carbonate and/or caprolactone, polyethylene glycol, and a random or block copolymer of ethylene oxide and propylene oxide.

In embodiments, the polyol component comprises polycaprolactone triol (MW 300).

Particulate Materials

In accordance with any of the embodiments described here, each individual reactive putty used to form the HPC can optionally contain a particulate material. In general, the particulate material consists of spherical particles. In embodiments, the spherical particles are in a size range of from about 1-700 microns average diameter. The spherical shape of the particulate material ensures that the HPC retains a smooth feel, rather than becoming lumpy or chunky which would be undesirable for the surgical uses described here.

In embodiments, the spherical particles comprise or consist of calcium phosphate particles having a density in the range of 2-3 g/cm$^3$ and a size in the range of 1-700 microns average diameter. The calcium phosphate particles may include one or more of tricalcium phosphate (TCP), tetracalcium phosphate, calcium pyrophosphate, hydroxyapatite, siliconized calcium phosphate, and a substituted calcium phosphate where the substitution is with magnesium, strontium, or silicate, for example, calcium phosphosilicate. The dense, spherical nature of the calcium phosphate particulate material serves to minimize the amount of liquid that can penetrate the HPC, thereby ensuring that the composition retains a suitable cohesiveness and does not become crumbly.

In embodiments, the particulate material comprises a first set of particles ranging in size from about 300-700 microns, or from about 300-650 microns, and a second set of particles ranging in size from 1-10 microns. In embodiments, the particles comprise or consist of calcium phosphate particles.

In embodiments, the particulate material may be selected from one or more of calcium phosphate, as described above, calcium sulfate, bone, partially or fully demineralized bone matrix (DBM), mineralized bone, and combinations of the foregoing.

In embodiments, the particulate material is selected from tricalcium phosphate, crystalline hydroxyapatite, and mixtures thereof.

In embodiments, the particulate material is selected from bone particles, DBM, tricalcium phosphate, crystalline hydroxyapatite, and mixtures thereof.

In embodiments, the particulate material is also an osteoconductive material. In embodiments, the particulate material supports or promotes the growth of bone into the HPC. As discussed above, the particulate material may comprise or consist of non-resorbable materials.

In embodiments, the particulate material comprises a carbonate or bicarbonate material. In embodiments, the carbonate or bicarbonate material comprises or consists of one or more of calcium carbonate, magnesium carbonate, aluminum carbonate, iron carbonate, zinc carbonate, calcium bicarbonate, and sodium bicarbonate.

In embodiments, the particulate material comprises or consists of bone, for example, one or more of demineralized bone, allograft bone, and/or autogenous bone.

In embodiments, the particulate material comprises or consists of calcium phosphate.

In embodiments, the particulate material comprises or consists of siliconized calcium phosphate, substituted calcium phosphates (e.g., with magnesium, strontium, or silicate), calcium pyrophosphate, hydroxyapatite, polymethyl methacrylate, glass-ionomer, absorbable phosphate glass, calcium sulfate, tricalcium phosphate (e.g., beta tricalcium phosphate), or any combination of the foregoing. Other examples include one or more poly ether ether ketones (e.g., PEEK), REPLACE (Cortek, Inc.), EXPANCEL (Akzo Nobel).

In embodiments, the particulate material comprises or consists of a ceramic material such as substituted calcium phosphates (e.g, silicate, strontium or magnesium substitution) or a glass such as bioglass.

In embodiments, the particulate material comprises graphene (available from Applied Graphene Materials and Thomas Swan, Ltd.), a single atomic layer of graphite that is electrically conductive, highly elastic, is about 100 times stronger than steel and which may be of value improving the quality of tissue healing and new bone stimulation.

The Optional Chain-Extender/Crosslinker Component

In embodiments, one or more chain extenders or crosslinkers, or both, are included in at least one of the individual reactive putties whose mixture forms the HPC. In embodiments, at least one of the individual reactive putties comprises a chain extender. In embodiments, the chain extender is present in one of the individual putties in an amount of from about 1-5 wt % (e.g., 1, 2, 3, 4, or 5 wt %), or from about 1-3 wt % (e.g., 1, 2, or 3 wt %), or from about 1-2 wt % of the putty.

In embodiments, the chain extender is a low molecular weight polyhydroxyl- and/or polyamine-terminated compound having a molecular weight in the range of 10 to 500 (e.g., 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 or 10-100, 10-200, 10-300, 10-400, 100-200, 100-300, 100-400, 100-500, 200-300, 200-400, 200-500, 300-400, 300-500, or 400-500) Daltons and a functionality of at least two. In embodiments, the chain extender is a short-chain diol or diamine.

Chain extenders having a functionality of three or more than three also function as crosslinkers. The degree of crosslinking can be controlled, for example, by varying the amount of crosslinker present. In embodiments, the crosslinker is a non-absorbable crosslinker selected from triethanolamine (TEA), trimethylolpropane, and QUADROL (BASF Corp.). In certain embodiments, the HPC is formed without crosslinkers.

The chain extender or crosslinker may be degradable or non-degradable. Preferably, at least one degradable chain extender is used. Suitable degradable chain extenders are described in U.S. 2009/0082540, which is incorporated herein by reference. Other suitable chain-extenders or crosslinkers include natural or synthetic aliphatic polyols. Suitable polydiols for use in the present disclosure include diol or diol repeating units with up to 8 carbon atoms. Non-limiting examples include 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol and combinations thereof.

In embodiments, the chain extender is a polyol selected from polyethylene glycol and polypropylene glycol having molecular weights of 500-10000 Daltons (e.g., 500, 1000, 1500, 2000, 2500, 3000, 3500, 4000, 4500, 5000, 5500, 6000, 6500, 7000, 7500, 8000, 8500, 9000, 9500, or 10000 or 500-1000, 500-5000, 500-10000, 1000-5000, 1000-10000, or 5000-10000). Other examples include CASPOL 1962 and CASPOL 5004. In embodiments, the polydiol component includes polydiols selected from polyethylene glycol and polypropylene glycol with molecular weights of 500-10000. In embodiments, the chain-extender component may comprise a non-degradable chain extender selected from 1,4-butanediol, 1,6-hexanediol, and diethylene glycol.

In embodiments, the chain extender is selected from glycerol, 1,4-butanediol, 1,6-hexanediol, diethylene glycol, cyclohexane dimethanol, and hydroquinone bis (2-hydroxyethyl) ether (HQEE), and mixtures thereof. In embodiments, the chain extender comprises or consists of 1,4-butanediol.

Other Optional Additives

As discussed above, the individual putties whose mixture forms the HPC may independently contain one or more additive materials. Preferred additives include one or more of a carboxylic acid ester of glycerin, such as glyceryl tripropionate or glyceryl triacetate (triacetin), a divalent metal salt of a fatty acid (e.g., calcium, magnesium, or zinc stearate), and the acetic acid ester of tocopherol, which may be referred to as tocopheryl acetate or Vitamin E acetate, and combinations of any or all of the foregoing.

The additives are generally present in at least one of the individual reactive putties, and one or more of the additives may be present in both putties of a pair, or in two or more putties of a multi-putty product. Generally, the additives are each present in amounts of no more than about 10 wt % (e.g., 0.1, 0.2, 0.3, 0.4, 0.5, 0.6, 0.7, 0.8, 0.9, 1, 2, 3, 4, 5, 6, 7, 8, 9, or 10 wt %) and generally in a range of from about 0.5-8 wt % (e.g., 0.5, 0.6, 0.7, 0.8, 0.9, 1, 2, 3, 4, 5, 6, 7, or 8 wt %) of an individual putty, or in the range of about 0.1-7 wt % (e.g., 0.1, 0.2, 0.3, 0.4, 0.5, 0.6, 0.7, 0.8, 0.9, 1, 2, 3, 4, 5, 6, or 7 wt %) based on the weight of the HPC.

In embodiments, the additive material may include blood clot-inducing agents such as prothrombin, thrombin, chitosan, carboxymethyl starch, oxidized cellulose, microcrystalline collagen, gelatin foam, collagen sponge or powder, fibrinogen, and fibrin.

In embodiments, the additive material may include a colorant. Non-limiting examples of colorants include gentian violet, D&C Violet #2, and D&C Green #6.

In embodiments, the additive material may include one or more of epinephrine, tannic acid, ferrous sulfate, and the double-sulfates of a trivalent metal and a univalent metal such as potassium aluminum sulfate and ammonium aluminum sulfate.

As discussed above, the additive component may also comprise one or more "cell openers." Non-limiting examples include ORTOGEL501 (Goldschmidt) and X-AIR (Specialty Polymers & Services). In embodiments, the cell openers are present in an amount in of from about 0.1% to 5% (e.g., 0.1, 0.2, 0.3, 0.4, 0.5, 0.6, 0.7, 0.8, 0.9, 1, 2, 3, 4, or 5%) by weight of the composition. In embodiments, the cell openers are present in an amount of from about 1% to 2% or 1% to 3% (e.g., 1, 2, or 3%) by weight of the HPC.

In embodiments, the additive component may also comprise one or more therapeutic agents. In embodiments, the one or more therapeutic agents is selected from an anti-cancer agent, an antimicrobial agent, an antibiotic, a local anesthetic or analgesic, a statin and an anti-inflammatory agent. In embodiments, the antibiotic is selected from a broad spectrum antibiotic, such as gentamicin, clindamycin, and erythromycin, or a gram positive and gram negative family antibiotic such as an ampicillin and a cephalosporin. In embodiments, the local anesthetic or analgesic is selected from lidocaine, bupivacaine, tetracaine, and ropivacaine. In embodiments, the local anesthetic or analgesic is selected from lidocaine, benzocaine and fentanyl (a potent non-opioid anesthetic). In embodiments, the one or more anti-inflammatory substances is selected from a non-specific anti-inflammatory such as ibuprofen and aspirin, or a COX-2 specific inhibitor such as rofecoxib and celeboxib.

In embodiments, the additive component may comprise an antioxidant. In embodiments, the antioxidant is selected from IRGANOX 1010 and IRGANOX 1035 (Ciba Geigy), and CYANOX 1790 and CYANOX 2777 (Cytec Industries). In embodiments, the antioxidant is present in an amount of from about 0.01% to 0.5% (e.g., 0.01, 0.02, 0.03, 0.04, 0.05, 0.06, 0.07, 0.08, 0.09, 0.1, 0.2, 0.3, 0.4, or 0.5% or 0.01-0.1, 0.01-0.2, 0.01-0.3, 0.01-0.4, 0.01-0.5, 0.1-0.2, 0.1-0.3, 0.1-0.4, 0.1-0.5, 0.2-0.3, 0.3-0.4, 0.3-0.5, or 0.4-0.5%) by weight of the HPC.

In embodiments, the additive component may comprise one or more growth factors, for example a bone morphogenic protein such as BMP-2 or BMP-7, platelet derived growth factor (PDGF), and epidermal growth factor (EGF).

In embodiments, the additive component may comprise a radiopaque agent.

Water

As discussed above, water at the surgical site of implantation reacts with isocyanate groups in the HPC generating carbamic acid which rapidly decomposes into gaseous carbon dioxide and the corresponding amine which in turn readily reacts with proximal unreacted isocyanate to form a urea linkage, thereby forming a polyurethane urea polymer. Also as discussed above, small amounts of water may be added to increase the rate of polymer formation. It should also be understood that even where there is no added water, water may nevertheless be present in small amounts. For example, certain commercially-available polyols comprise a mixture of the polyol and a small amount of water. In addition, certain optional particulate materials as described herein, such as calcium carbonate, may comprise bound water. Formulating the compositions in an atmosphere that contains moisture may also result in the incorporation of water into the composition. In embodiments, the compositions are prepared under a nitrogen purge that comprises a desired amount of moisture, thereby controlling the water content of the compositions.

In embodiments, the compositions contain no added water and are essentially anhydrous. For example, where the HPC is formed ex vivo and used to make a custom implant, the resulting custom implant will be essentially anhydrous. As a consequence, the polymer will be a polyurethane polymer if only polyols and no polyamines are used, rather than a polyurethane urea polymer.

In addition to the isocyanate-based compositions discussed above, the disclosure also provides compositions of similar utility made from other materials. For example, provided are multi-putty compositions formed from cyanoacrylate and methylidene malonate esters, magnesium phosphates, polyethylene glycols, poly (methyl methacrylate), and epoxides. Any of the optional additive materials described above may also be incorporated into these compositions, which are described in more detail below.

Cyanoacrylate- and Methylidene Malonate Ester-Based Compositions

In embodiments, the HPC cures into a fully hardened polymer composition comprising either methylidene malonate or alkyl cyanoacrylate esters such as octyl cyanoacrylate polymers. The first reactive putty may comprise, for example, either diethylmethylidene malonate or octyl cyanoacrylate monomer, a viscosity builder such as a minor amount of poly(diethylmethylidine malonate esters) or poly (octylcyanoacrylate), a free radical polymerization inhibitor component, e.g., hydroquinone, an acid component to inhibit based-catalyzed polymerization, e.g., sulfur dioxide and an optional anhydrous particulate component. The one or more additional putties may comprise the viscosity builder of the first putty and, optionally, a particulate material, and one or more additional optional additives. In embodiments, the one or more additional optional additives is selected from a bone-growth promoting agent, a colorant, a therapeutic agent and a radiopaque agent. In embodiments, the therapeutic agent is selected from one or more of an anti-cancer agent, an antimicrobial agent, an antibiotic, a local anesthetic or analgesic, and an anti-inflammatory agent. In embodiments, the bone growth promoting agent is selected from bone morphogenic protein and demineralized bone matrix, and mixtures thereof. In embodiments, the bone-growth promoting agent is an osteopromotive recombinant protein selected from the group consisting of bone morphogenic proteins, platelet derived growth factor, transforming growth factor beta, epidermal growth factor, NELL and UCB-1, and combinations thereof.

In one embodiment, the composition comprises two putty components, A and B; and putty A comprises 20-50 wt % (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% or 20-25, 20-30, 20-35, 20-40, 20-45, 25-30, 25-35, 25-40, 25-45, 25-50, 30-35, 30-40, 30-45, 30-50, 35-40, 35-45, 35-50, 40-45, 40-50, or 45-50%) of the diethylmethylidene malonate or octyl cyanoacrylate monomer, 1-15 wt % (e.g., 1, 2, 3, 4, 5, 6, 7, 8, 9, 10, 11, 12, 13, 14, or 15% or 1-5, 1-10, 5-10, 5-15, or 10-15%) of the viscosity building component, 0-75 wt % (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% or 0-5, 0-10, 0-15, 0-20, 0-25, 0-30, 0-35, 0-40, 0-45, 0-50, 0-55, 0-60, 0-65, 0-70, 5-10, 5-15, 5-20, 5-25, 5-30, 5-35, 5-40, 5-45, 5-50, 5-55, 5-60, 5-65, 5-70, 5-75, 10-15, 10-20, 10-25, 10-30, 10-35, 10-40, 10-45, 10-50, 10-55, 10-60, 10-65, 10-70, 10-75, 15-20, 15-25, 15-30, 15-35, 15-40, 15-45, 15-50, 15-55, 15-60, 15-65, 15-70, 15-75, 20-25, 20-30, 20-35, 20-40, 20-45, 20-50, 20-55, 20-60, 20-65, 20-70, 20-75, 25-30, 25-35, 25-40, 25-45, 25-50, 25-55, 25-60, 25-65, 25-70, 25-75, 30-35, 30-40, 30-45, 30-50, 30-55, 30-60, 30-65, 30-70, 30-75, 35-40, 35-45, 35-50, 35-55, 35-60, 35-65, 35-70, 35-75, 40-45, 40-50, 40-55, 40-60, 40-65, 40-70, 40-75, 45-50, 45-55, 45-60, 45-65, 45-70, 45-75, 50-55, 50-60, 50-65, 50-70, 50-75, 55-60, 55-65, 55-70, 55-75, 60-65, 60-70, 60-75, 65-70, 65-75, or 70-75%) particulate material, based upon total weight of putty A, a radical polymerization inhibitor component and an acidic polymerization inhibitor component; putty B comprises 3-40 wt (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40% or 3-5, 3-10, 3-15, 3-20, 3-25, 3-30, 3-35, 5-10, 5-15, 5-20, 5-25, 5-30, 5-35, 5-40, 10-15, 10-20, 10-25, 10-30, 10-35, 10-40, 15-20, 15-25, 15-30, 15-35, 15-40, 20-25, 20-30, 20-35, 20-40, 25-30, 25-35, 25-40, 30-35, 30-40, or 35-40%) of the viscosity building component, and, optionally, 0-85 wt % (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85% or 0-5, 0-10, 0-15, 0-20, 0-25, 0-30, 0-35, 0-40, 0-45, 0-50, 0-55, 0-60, 0-65, 0-70, 0-75, 0-80, 5-10, 5-15, 5-20, 5-25, 5-30, 5-35, 5-40, 5-45, 5-50, 5-55, 5-60, 5-65, 5-70, 5-75, 5-80, 5-85, 10-15, 10-20, 10-25, 10-30, 10-35, 10-40, 10-45, 10-50, 10-55, 10-60, 10-65, 10-70, 10-75, 10-80, 10-85, 15-20, 15-25, 15-30, 15-35, 15-40, 15-45, 15-50, 15-55, 15-60, 15-65, 15-70, 15-75, 15-80, 15-85, 20-25, 20-30, 20-35, 20-40, 20-45, 20-50, 20-55, 20-60, 20-65, 20-70, 20-75, 20-80, 20-85, 25-30, 25-35, 25-40, 25-45, 25-50, 25-55, 25-60, 25-65, 25-70, 25-75, 25-80, 25-85, 30-35, 30-40, 30-45, 30-50, 30-55, 30-60, 30-65, 30-70, 30-75, 30-80, 30-85, 35-40, 35-45, 35-50, 35-55, 35-60, 35-65, 35-70, 35-75, 35-80, 35-85, 40-45, 40-50, 40-55, 40-60, 40-65, 40-70, 40-75, 40-80, 40-85, 45-50, 45-55, 45-60, 45-65, 45-70, 45-75, 45-80, 45-85, 50-55, 50-60, 50-65, 50-70, 50-75, 50-80, 50-85, 55-60, 55-65, 55-70, 55-75, 55-80, 55-85, 60-65, 60-70, 60-75, 60-80, 60-85, 65-70, 65-75, 65-80, 65-85, 70-75, 70-80, 70-85, 75-80, 75-85, or 80-85%) of particulate material, based upon the total weight of putty B, and one or more optional therapeutic agents or growth promoting agents. In one embodiment, the viscosity building component comprises polymerized monomer, the radical induced polymerization inhibitor component comprises or consists of hydroquinone and the acid induced polymerization inhibitor component comprises or consists of sulfur dioxide.

In one embodiment, the composition comprises two putty components, A and B, putty A comprising a methylidene malonate ester and a poly(methylidene malonate ester) in amounts ranging from 30 to 70 wt % (e.g., 30-65, 30-60, 30-55, 30-50, 30-45, 30-40, 30-35, 35-70, 35-65, 35-60, 35-55, 35-50, 35-45, 35-40, 40-70, 40-65, 40-60, 40-55, 40-50, 40-45, 45-70, 45-65, 45-60, 45-55, 45-50, 50-70, 50-65, 50-60, 50-55, 55-70, 55-65, 55-60, 60-70, 60-65, or 65-70, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70%) and putty B comprising poly(methylidenemalonate ester), in amounts ranging from 30 to 100 wt % (e.g., 30-95, 30-90, 30-85, 30-80, 30-75, 30-70, 30-65, 30-60, 30-55, 30-50, 30-45, 30-40, 35-100, 35-95, 35-90, 35-85, 35-80, 35-75, 35-70, 35-65, 35-60, 35-55, 35-50, 35-45, 35-40, 40-100, 40-95, 40-90, 40-85, 40-80, 40-75, 40-70, 40-65, 40-60, 40-55, 40-50, 40-45, 45-100, 45-95, 45-90, 45-85, 45-80, 45-75, 45-70, 45-65, 45-60, 45-55, 45-50, 50-100, 50-95, 50-90, 50-85, 50-80, 50-75, 50-70, 50-65, 50-60, 50-55, 55-100, 55-95, 55-90, 55-85, 55-80, 55-75, 55-70, 55-65, 55-60, 60-100, 60-95, 60-90, 60-85, 60-80, 60-75, 60-70, 60-65, 65-100, 65-95, 65-90, 65-85, 65-80, 65-75, 65-70, 70-100, 70-95, 70-90, 70-85, 70-80, 70-75, 75-100, 75-95, 75-90, 75-85, 75-80, 80-100, 80-95, 80-90, 80-85, 85-100, 85-95, 85-90, 90-100, 90-95, or 95-100, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%), wherein the amounts are based upon total weight of the composition.

In one embodiment, the composition comprises two putty components, A and B, putty A comprising or consisting of a cyanoacrylate ester in amounts ranging from 30 to 70 wt % (e.g., 30-65, 30-60, 30-55, 30-50, 30-45, 30-40, 30-35, 35-70, 35-65, 35-60, 35-55, 35-50, 35-45, 35-40, 40-70, 40-65, 40-60, 40-55, 40-50, 40-45, 45-70, 45-65, 45-60, 45-55, 45-50, 50-70, 50-65, 50-60, 50-55, 55-70, 55-65, 55-60, 60-70, 60-65, or 65-70, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70%) and a poly (cyanoacrylate) ester in amounts ranging from 70 to 30 wt % (e.g., 70-35, 70-40, 70-45, 70-50, 70-55, 70-60, 70-65, 65-30, 65-35, 65-40, 65-45, 65-50, 65-55, 65-60, 60-30, 60-35, 60-40, 60-45, 60-50, 60-55, 55-30, 55-35, 55-40, 55-45, 55-50, 50-30, 50-35, 50-40, 50-45, 45-30, 45-35, 45-40, 40-30, 40-35, 35-30, for example, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30%) and putty B comprising poly(cyanoacrylate) ester in amounts ranging from 97 to 100 wt % (e.g., 97, 98, 99, or 100%), wherein the amounts are based upon total weight of the composition.

In another embodiment, a first putty is formed from polyisobutyl cyanoacrylate with 0.1-1 wt % (e.g., 0.1-0.5 or 0.5-1, for example, 0.1, 0.2, 0.3, 0.4, 0.5, 0.6, 0.7, 0.8, 0.9, or 1%) hydroquinone and 0.25-0.5 wt % (e.g., 0.25-0.3, 0.25-0.35, 0.25-0.4, 0.25-0.45, 0.3-0.35, 0.3-0.4, 0.3-0.45, 0.3-5, 0.35-0.4, 0.35-0.45, 0.35-0.5, 0.4-0.45, 0.4-0.5, 0.45-0.5, for example, 0.25, 0.26, 0.27, 0.28, 0.29, 0.3, 0.31, 0.32, 0.33. 0.34, 0.35, 0.36, 0.37, 0.38, 0.39, 0.4, 0.41, 0.42, 0.43, 0.44, 0.45, 0.46, 0.47, 0.48, 0.49, or 5%) sulfur dioxide as stabilizers and a second putty is formed from 97-99 wt % (e.g., 97, 98, or 99%) polyisobutyl cyanoacrylate with 0.1-3 wt % (e.g., 0.1-0.5, 0.1-1, 0.1-1.5, 0.1-2, 0.1-2.5, 0.1-3, 0.5-1, 0.5-1.5, 0.5-2, 0.5-2.5, 0.5-3, 1-1.5, 1-2, 1-2.5, 1-3, 1.5-2, 1.5-2.5, 1.5-3, 2-2.5, 2-3, or 2.5-3, for example, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3%) benzoyl peroxide and/or ferric chloride as radical or ionic polymerization initiators, respectively. The putties must be kept dry. These two putties cannot be hand kneaded because the activated cyanoacrylate will adhere to surgical gloves. Instead, these putties may be dispensed from foil pouches, tubes, syringes and/or cartridges connected with a mixing device. Polymerization time can be controlled by balancing the amounts of stabilizers in the first putty with the initiators (neutralizers) in the second putty.

In another embodiment, a first aqueous putty is formed from a 7% carboxymethyl cellulose (CMC) solution and a second aqueous putty is formed from a 7% chitosan solution. When the two are combined to form an HPC, the resulting HPC is a semisolid hydrogel putty which may be used as a soft tissue hemostat and adhesive. Additional additives may be incorporated to one or both putties, for example antimicrobials, analgesics, anesthetics, chemotherapeutics, anti-inflammatories, growth factors, radiopaques, hemostatic agents, and/or statins, etc. To control hardness and rate of absorption, the CMC putty may be subjected to ionic cross-linking with calcium chloride and the chitosan putty may be covalently crosslinked with a biocompatible diisocyanate to form a polyurea. Alternatively, the HPC hydrogel putty may be crosslinked with a biocompatible carbodiimide to form an amide-based more rigid putty composition. In additional embodiments, 25 wt % calcium phosphate powder may be added to one or both of the putties to form a material suitable as a bone void filler.

Magnesium Phosphate-Based Compositions

In embodiments, the HPC cures into a fully hardened non-polymeric composition. In accordance with this embodiment, a first putty comprises potassium dihydrogen phosphate, magnesium oxide, and a calcium containing compound such as, e.g., tricalcium phosphate and/or hydroxyapatite ($Ca_{10}(PO_4)_6(OH)_2$ suspended in one or a mixture of anhydrous, nontoxic, partially water-miscible, inert suspension vehicles, for example one or a mixture of two or more of triacetin, a Pluronic™ (poloxamer) such as Pluronic™ L-35, and acetyl triethyl citrate, or similar liquids. A nontoxic viscosity building agent may be added, if necessary. The one or more additional putties comprises water, and one or a mixture of two or more viscosity building agents. In one embodiment, the viscosity building agent or agents are selected from sodium carboxymethyl cellulose, sodium alginate, Carbomer™, carrageenan, aluminum silicate (Bentonite™), gelatin, collagen, and chitosan. In one embodiment, the viscosity building agent is present at about 75-85 wt % (i.e., 75, 76, 77, 78, 79, 80, 81, 82, 83, 84, or 85% or 75-80 or 80-85%). The second putty component may also optionally comprise a particulate material. In one embodiment the particulate material is selected from tricalcium phosphate and hydroxyapatite, or mixtures thereof. In one embodiment, the one or more additional second components may also optionally comprise one or more additional additives selected from a colorant, an antioxidant, and a therapeutic agent, for example, a statin.

In one embodiment, the therapeutic agent is selected from one or more of an anti-cancer agent, an antimicrobial agent, an antibiotic, a local anesthetic or analgesic, a statin and an anti-inflammatory agent. In one embodiment, the one or more additional putties may further comprise a bone-growth promoting agent.

PEG-Based Compositions

The present disclosure also provides PEG-based multi-putty compositions. In embodiments, the uncombined putties are water soluble or dispersable putties. In embodiments, the PEG-based multi-putty adhesive composition comprises two separate, individual reactive putties. In one embodiment, the first putty comprises a mixture of PEG monostearate and PEG containing tetracalcium phosphate, phosphoserine and dry buffer-producing powder and the second putty comprises a mixture of PEG monostearate and PEG containing fibrous or powdered absorbable polyester polymer, e.g. PGA or fibrous or powdered nonabsorbable polyester polymer, e.g. polyethyleneterephthalate. When the separate reactive putties are combined into a homogenous mass and hydrated, e.g., with saline and/or by placing on wet tissue, the resulting composition forms an adhesive that hardens into a cement.

In another embodiment, the first putty is acidic and comprises polyethylene glycol monostearate and polyethylene glycol that contains an acidic phosphate salt, such as monocalcium phosphate monohydrate, an acidic pH buffering agent, such as citric acid, an optional humectant, such as glycerol and a synthetic polymer thickening agent, such as polyvinylpyrrolidone and/or sodium carboxymethyl cellulose and/or hypromellose. The second putty is basic and contains water, a basic calcium phosphate, such as tetracalcium phosphate, a surfactant, such as polysorbate 80 and, optionally, a thickening agent, such as polyvinylpyrrolidone and/or sodium carboxymethyl cellulose and/or hypromellose. Either or both putties may optionally contain an osteoconductive ceramic, such as hydroxyapatite. When the separate reactive putties are combined into a homogenous mass and hydrated with saline or placed on wet tissue, the resulting composition forms an adhesive that hardens into a cement.

The disclosure also provides a general method for avoiding the mixing of aqueous components with dry reactants to form a settable composition. In embodiments, the solid reactants are separated into two groups that remain stable if kept anhydrous. Group 1, for example, may contain putty-like dispersions of powdered tetracalcium phosphate, phosphoserine and a buffer precursor, such as a dry phosphate or carbonate mixture that, when dissolved, will provide a pH of 7-8. The powders may be dispersed in anhydrous PEG stearate/polyalkylene oxide mixtures. Group 2 may contain PEG stearate/polyalkylene oxide putty-like dispersions of fibers or powder prepared from an absorbable polyester, such as polyglycolic acid or a nonabsorbable polyester, such as polyethyleneterephthalate, depending upon whether the adhesive-cement is designed to be absorbable or nonabsorbable in the body after implantation. When the two putties are mixed and sufficiently hydrated, a settable, initially adhesive cement is formed.

The present disclosure also provides a multi-putty settable surgical adhesive composition comprising two separate, individual reactive putties, one putty comprising tetracalcium phosphate powder in an aqueous vehicle and the second putty comprising phosphoserine and polyester in a non-aqueous vehicle. In embodiments, the aqueous vehicle is any water-based vehicle. In embodiments, the aqueous vehicle is saline, or other buffered salt solution, such as phosphate buffered saline. In embodiments, the non-aqueous vehicle is PEG or a fatty acid ester of PEG.

Lally et al. describe a hemostatic biomaterial (US 2012/0308552) based on combining a mixture of dry powders with saline to form a bone-hemostatic, phosphate-based aqueous slurry. Preparing such a slurry is inconvenient and the present disclosure, involving combining putties in which the components are dispersed, avoids the inconvenient powder/saline preparation and also provides a putty-like composition that is more easily applied and is more adherent to bone than is an aqueous slurry.

In embodiments, a first reactive putty comprises 35 wt % polyethyleneglycol monostearate, 10 wt % polyethylene glycol, 30 wt % tetracalcium phosphate, 20 wt % phosphoserine and 5 wt % dry phosphate buffer precursor powder and a second reactive putty comprises 35 wt % polyethyleneglycol monostearate, 30 wt % polyethylene glycol, 30 wt % micronized polyglycolic acid (for absorbable cements) or, 30 wt % micronized polyethyleneterephthalate (for nonabsorbable cements), 5 wt % dry phosphate buffer precursor powder.

Poly (Methyl Methacrylate) (PMMA) Based Compositions

The present disclosure also provides multi-putty surgical adhesive compositions consisting of at least two separate, individual reactive putties wherein the reactive components comprise liquid acrylate and methacrylate monomers and powdered polyacrylate and polymethacrylate polymers. In embodiments, the multi-putty adhesive composition comprises two separate, individual reactive putties. In one embodiment, the first putty comprises one or more liquid acrylate and methacrylate monomers and polyacrylate and polymethacrylate polymers with a solubilizing vehicle such as ethyl acetate or N-methylpyrrolidone, to form a putty. The second putty comprises a free radical source, such as benzoyl peroxide, or an ionic source, such as ferric acetate, and one or more powdered polyacrylate and polymethacrylate polymers dissolved or suspended in an inert liquid vehicle, such as ethyl acetate or N-methylpyrrolidone, to form a putty. When the two putties are combined, polymerization of the monomers in the first putty is initiated by the free radical or ionic source in the second putty which avoids the more difficult mixing together of solids and liquids.

In an embodiment, a first putty comprises 50 wt % methyl methacrylate, 20 wt % methyl acrylate and 10 wt % polymethyl acrylate and 10 wt % polymethylmethacrylate as thickener polymers dissolved in 10 wt % N-methylpyrrolidone, and optional additives selected from one or more of a colorant (0.25 wt %) and osteogenic ceramic (5 wt %) to reinforce the polymer and stimulate bone growth; and a second putty comprises 5 wt % benzoyl peroxide, 10 wt % polymethyl acrylate and 10 wt % polymethyl methacrylate as thickeners dissolved in N-methylpyrrolidone.

Epoxide Based Compositions

The disclosure also provides multi-putty settable surgical materials based on epoxides as the reactive group. In one embodiment, the polymer system is based upon reactive epoxide groups which form catalytic homopolymerizations or, alternatively, copolymers by reaction with curatives or hardeners such as polyfunctional amines, acids, phenols, alcohols, anhydrides or thiols and combinations thereof. As with PMMA, curing of epoxy resins is exothermic and should be controlled to avoid adverse thermal effects on tissue. Aliphatic and cycloaliphatic epoxides react more slowly than do aromatics and exhibit lower exotherms.

While uncured epoxy resins are potentially irritating and sensitizing, cured polymers are essentially non-toxic and have been used, for example, to encapsulate implantable cardiac pacemakers. (See U.S. Pat. Nos. 3,700,628 and 3,924,640). Earlier reports of cured epoxy carcinogenicity now are attributed to the presence of carcinogenic epichlorohydrin which is no longer used for preparing most epoxy resins.

In one embodiment, an epoxy resin such as triglycidal-p-aminophenol is liquid at room temperature and has relatively high reactivity. It may be cured with a cycloaliphatic amine catalyst such as dicyclohexyl amine. The advantage of this embodiment over prior art is that both the liquid epoxy resin and the curing components are converted to putty-like consistencies by the addition of micronized solid fillers such as phosphate salts and/or ceramics or by non-reactive, finely ground polymers such as PVP or ground previously formed epoxy-based polymers. Aseptically hand kneading such sterile putties together provides a surgically useful initially adhesive cement.

Copolymers made with a hydrolysable polyol such as, e.g., the diglycolate ester of 1,3-propane diol in a stochiometrically correct ratio with the epoxy resin will provide an absorbable version of the surgical device. The epoxide resin backbone also can be made with hydrolysable linkages such as esters, e.g., glycidyl-$CH_2$—$CH_2$—$CO_2$—$CH_2$—$CH_2$-glycidyl, to form absorbable polymers which have been further enhanced regarding absorbability be combining hydrolysable epoxy resins with hydrolysable polyols.

In one embodiment, the disclosure provides a multi-putty settable surgical composition comprising two separate, individual reactive putties, a first putty comprising an aliphatic and/or aromatic polyglycidyl epoxy resin of sufficient molecular weight to provide a putty-like consistency and a second putty containing an optional thickener and a polyfunctional primary and/or secondary amine, polyfunctional anhydride, polyfunctional phenol or polyfunctional thiol. In one embodiment, the disclosure provides a surgical composition formed by combining the two separate individual reactive putties into a single homogenous mass, wherein the composition is absorbable or nonabsorbable.

In an embodiment, a first reactive putty comprises 60-80 wt % (e.g., 60-75, 60-70, 60-65, 65-80, 65-75, 65-70, 70-80, 70-75, or 75-80, for example, 60, 61, 62, 63, 64, 65, 66, 67, 68, 69, 70, 71, 72, 73, 74, 75, 76, 77, 78, 79, or 80%) triglycidal-p-amino phenol and 20-40 wt % (e.g., 20-35, 20-30, 20-25, 25-40, 25-35, 25-30, 30-40, 30-35, or 35-40, for example, 20, 21, 22, 23, 24, 25, 26, 27, 28, 29, 30, 31, 32, 33, 34, 35, 36, 37, 38, 39, or 40%) of a thickener comprised of micronized polyvinyl pyrrolidone or of micronized calcium phosphate, and a second reactive putty comprises 60-80 wt % (e.g., 60-75, 60-70, 60-65, 65-80, 65-75, 65-70, 70-80, 70-75, or 75-80, for example, 60, 61, 62, 63, 64, 65, 66, 67, 68, 69, 70, 71, 72, 73, 74, 75, 76, 77, 78, 79, or 80%) dicyclohexyl amine and 20-40 wt % (e.g., 20-35, 20-30, 20-25, 25-40, 25-35, 25-30, 30-40, 30-35, or 35-40, for example, 20, 21, 22, 23, 24, 25, 26, 27, 28, 29, 30, 31, 32, 33, 34, 35, 36, 37, 38, 39, or 40%) of a thickener comprising micronized hydroxyapatite with optional additives selected from tocopheryl acetate (5 wt %), antimicrobial agents (2 wt %) and a porogen such as fructose crystals (10 wt %). Alternatively, the second reactive putty may comprise 60-80 wt (e.g., 60-75, 60-70, 60-65, 65-80, 65-75, 65-70, 70-80, 70-75, or 75-80, for example, 60, 61, 62, 63, 64, 65, 66, 67, 68, 69, 70, 71, 72, 73, 74, 75, 76, 77, 78, 79, or 80%) of a co-monomer of the diglycidal ester of ethylene glycol-beta-hydroxypropionate and 20-40 wt % (e.g., 20-35, 20-30, 20-25, 25-40, 25-35, 25-30, 30-40, 30-35, or 35-40, for example, 20, 21, 22, 23, 24, 25, 26, 27, 28, 29, 30, 31, 32, 33, 34, 35, 36, 37, 38, 39, or 40%) of a thickener comprised of micronized calcium phosphate, with an optional porogen such as sugar fibers (10 wt %).

Methods

As discussed above, the HPC material described here is a highly versatile surgical material. Its cohesiveness and adhesiveness allow it to be formed into suitable shapes and used in place of conventional surgical hardware such as a spacer, cage, wrap, tape, cuff, shim, plate, dowel, bridge, rod, scaffold, pin, screw, tine, etc. The HPC material can also be used generally for fixation and/or stabilization at multiple points and in multiple planes. The HPC material may also be applied to stabilize traditional surgical hardware, for example by pressing the HPC into drilled or tapped holes followed by applying a pin, screw, tine, etc., or by applying the HPC over the surface of the hardware, such as plate.

In its initial solid putty form, the HPC is highly adhesive, making it suitable for use as an adhesive or glue in the reapproximation of adjacent fragments of bone or more generally in the repair of fragmented bone. As the HPC sets, it solidifies into a hardened cement-like material of sufficient mechanical strength to provide stabilization, for example of a fracture line, e.g., in the manner of an anchor, screw, or tine. The initial form of the HPC is also sufficiently elastic to enable it to be stretched into the form of a wrap, tape, or cuff and applied for example, around the circumference of a fracture, acting to stabilize the fracture line. In this sense, the HPC material may also be formed into an internal orthopedic cast.

In general, in accordance with the methods described here, the HPC is formed intraoperatively by mixing two or more separate reactive putties, as described above, either by hand or using a suitable device, but in some embodiments a single putty may be used without prior mixing with a paired putty, for example as discussed in connection with the "moisture cure embodiment". Thus, although the methods exemplified below generally begin with forming the HPC from two or more reactive putties, it should also be understood that in some embodiments a single putty may be used.

It should also be understood that, in each of the exemplary methods discussed below, the step of forming the HPC from two or more reactive putties may be conducted more than once, using different sets of reactive putties. For example, a first portion of HPC may be formed using a different set of reactive putties than that used to from a second portion of HPC, and so on, where two or more portions of HPC are used in the method. In addition, or alternatively, a portion of HPC may be divided into one or more additional portions for use in the method.

In accordance with any of the embodiments of the methods described here, the methods may further comprise a step of removing excess HPC material from the surgical site.

Also in accordance with any of the embodiments of the methods described here, rigid bone fixation may be completed in about 24 hours, and the HPC may be replaced by autogenous bone within about 3-24 months.

In embodiments, the disclosure provides methods for the re-approximation of cut or fractured bone, including long bones, bones of the hands or feet, and cranial bones, including the repair of cranial defects and cranioplasty applications, as well as methods for the repair and reconstruction of the sternum. Preferably, the surgical procedures described here are practiced on humans, but they may also be used on other mammals such as a dog, a cat, a horse, a cow, a pig, or a non-human primate.

The following are exemplary methods of using the compositions described here to improve common surgical techniques for bone repair and reconstruction and are not meant to be limiting.

In accordance with any of the embodiments of the methods described here, the two or more individual reactive putties which when combined form the HPC may consist of two reactive putties. In embodiments, the two reactive putties each comprise a prepolymer in an amount in the range of from about 3-8 wt % (e.g., 3-5, 3-6, 3-7, 3-8, 4-6, 4-7, 4-8, 5-7, 5-8, or 6-8, for example, 3, 4, 5, 6, 7, or 8 wt %) and a particulate material in an amount in the range of from about 50-90 wt % (e.g., 50-85, 50-80, 50-75, 50-70, 50-65, 50-60, 55-90, 55-85, 55-80, 55-75, 55-70, 55-65, 55-60, 60-90, 60-85, 60-80, 60-75, 60-70, 60-65, 65-90, 65-85, 65-80, 65-75, 65-70, 70-90, 70-85, 70-80, 70-75, 75-90, 75-85, 75-80, 80-90, 80-85, or 95-90, for example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %). It should be understood that although the amount of prepolymer and particulate material in each putty is within these ranges, the amounts in each putty need not be the same. In addition, in accordance with this embodiment, one of the putties further comprises excess isocyanate in amounts of from about 25-35 wt % (e.g., 25-30, or 30-35, for example, 25, 26, 27, 28, 29, 30, 31, 32, 33, 34, or 35 wt %), and the other comprises excess polyol and/or polyamine, in amounts of from about 1-3 wt % (e.g., 1, 2, or 3 wt %). One or both putties may further comprise an optional chain extender and one or more optional additives, as described above. Preferred isocyanates include an absorbable lactyl-bridged diisocyanate (e.g., ALD), a lactylglycolyl bridged diisocyanate and lysine diisocyante. Preferred polyols include polycaprolactone triol, polypropyleneglycoltriol, and 1.4 butane diol. Preferred particulate materials include tricalcium phosphate and hydroxyapatite. Preferred additives include one or more of a carboxylic acid ester of glycerin, such as glyceryl tripropionate or glyceryl triacetate (triacetin), a divalent metal salt of a fatty acid (e.g., calcium, magnesium, or zinc stearate), and the acetic acid ester of tocopherol, which may be referred to as tocopheryl acetate or Vitamin E acetate, and combinations of any or all of the foregoing. In embodiments, the HPC material formed from the combination of the putties comprises from about 20-30 wt % (e.g., 20-25, or 25-30, for example, 20, 21, 22, 23, 24, 25, 26, 27, 28, 29, or 30 wt %) polymer and from about 60-75 wt % (e.g., 60-70, 60-65, 65-75, or 65-70, for example, 60, 61, 62, 63, 64, 65, 66, 67, 68, 69, 70, 71, 72, 73, 74, or 75 wt %) particulate material, with the remainder being made up of one or more additives. In embodiments, the one or more additives is selected from triacetin, calcium stearate, tocopheryl acetate, an N-alkylpyrrolidone, trimethylamine, triethanolamine, chitosan, alpha-polylysine, a colorant, an antioxidant, and a therapeutic agent.

In embodiments, the particulate component ranges from about 60-75 wt % (e.g., 60-70, 60-65, 65-75, or 65-70, for example, 60, 61, 62, 63, 64, 65, 66, 67, 68, 69, 70, 71, 72, 73, 74, or 75 wt %), the total additive component ranges from about 3-10 wt % (e.g., 3-5, 3-6, 3-7, 3-8, 3-9, 3-10, 4-6, 4-7, 4-8, 4-9, 4-10, 5-7, 5-8, 5-9, 5-10, 6-8, 6-9, 6-10, 7-9, 7-10, or 8-10, for example, 3, 4, 5, 6, 7, 8, 9, or 10 wt %), or from about 5-15 wt % (e.g., 5-10 or 10-15, for example, 5, 6, 7, 8, 9, 10, 11, 12, 13, 14, or 15 wt %), based on the total weight of the HPC, and the additive component comprises 1,4-butanediol, triacetin, calcium stearate, and tocopheryl acetate. In accordance with this embodiment, the HPC remains easily spreadable, hand-moldable, and/or extrudable for a period of time that is at least about 5-10 minutes (e.g, 5-7, 5-8, 5-9, 5-10, 6-8, 6-9, 6-10, 7-9, 7-10, or 8-10, for example, 5, 6, 7, 8, 9, or 10 minutes), after which time it hardens into a form that resists mechanical deformation and is suitable for drilling or tapping without cracking or breaking within about 20 minutes.

In embodiments, the particulate component ranges from about 70-85 wt % (e.g., 70-80, 75-85, 75-80, for example, 70, 71, 72, 73, 74, 75, 76, 77, 78, 79, 80, 81, 82, 83, 84, or 85 wt %), the total additive component ranges from about 5-20 wt % (e.g., 5-15, 5-10, 10-20, 10-15, or 15-20, for example, 5, 6, 7, 8, 9, 10, 11, 12, 13, 14, 15, 16, 17, 18, 19, or 20 wt %), or from about 7-15 wt % (e.g., 7-9, 7-10, 7-11, 7-12, 7-13, 7-14, 7-15, 8-10, 8-11, 8-12, 8-13, 8-14, 8-15, 9-11, 9-12, 9- 13, 9-14, 9-15, 10-12, 10-13, 10-14, 10-15, 11-13, 11-14, 11-15, 12-14, 12-15, or 13-15, for example, 7, 8, 9, 10, 11, 12, 13, 14, or 15 wt %), based on the total weight of the HPC, and the additive component comprises triethanolamine, an N-alkylpyrrolidone (e.g., N-methylpyrrolidone), triacetin, calcium stearate, and tocopheryl acetate. In accordance with this embodiment, the HPC is "fast-setting" and remains easily spreadable, hand-moldable, and/or extrudable for a period of time that is at least about 30 seconds to two minutes, after which time it hardens into a form that resists mechanical deformation and is suitable for drilling or tapping without cracking or breaking within about 5-10 minutes (e.g., 5, 6, 7, 8, 9, or 10 minutes).

In accordance with any of the methods described here, in addition to or as an alternative for some applications to forming the HPC from two or more reactive putties, an individual putty may be molded or shaped into an appropriate implant and placed in situ to harden by reacting with water at the site of implantation. In accordance with this embodiment, which may be referred to as the "moisture cure" embodiment, the time to hardening may be relatively longer than when the HPC is formed from the reactive putties. In accordance with the moisture cure embodiment, the individual reactive putty may comprise an isocyanate component that is from about 30-40 wt % (e.g., 30-35 or 35-30, for example, 30, 31, 32, 33, 34, 35, 36, 37, 38, 39, or 40 wt %) of the putty, a polyol component that is about 1-5 wt % (e.g., 1-3, 1-4, 2-4, 2-5, or 3-5, for example, 1, 2, 3, 4, or 5 wt %) of the putty, and a particulate component that is about 50-60 wt % (e.g., 50-55, or 55-60, for example, 50, 51, 52, 53, 54, 55, 56, 57, 58, 59, or 60 wt %) of the putty.

In accordance with any of the embodiments of the methods described here, and as described above, one or more optional additives may be included in at least one of the individual reactive putties used to form the HPC. In embodiments, the one or more optional additives are selected from growth factors, including bone morphogenic protein, analgesics, anesthetics, antioxidants, antibiotics, and/or antimicrobials, each of which is described in more detail above.

Custom Implants

In accordance with any of the embodiments of the methods described here, the methods may optionally comprise forming a custom implant using the HPC. In embodiments, the custom implant may be formed using a mold (e.g., to form a plate, screw, rod, etc.) or a shape stamp or cutter. The HPC may also be hand molded and shaped intraoperatively to fill bony deficits, such as to replace a portion of the cranium or acetabulum. This eliminates the need to design a custom implant which requires imaging and manufacturing time, delaying the time to surgical repair. The HPC could be pressed into the edges of the surrounding bone and allowed to harden. Alternatively the implant could be shaped and hardened outside of the body, intraoperatively, machined to the desired geometry and secured with hardware (conventional or HPC-based).

In embodiments, the custom implant may be formed using digital information describing the anatomical defect to be repaired, or the anatomical part to be created. Such digital information may be obtained from any suitable source including, for example, medical imaging equipment (e.g., ultrasound, X-ray, magnetic resonance imaging, CT scan, etc.). In embodiments, the digital information is used to program a Computer Numeric Controlled (CNC) machine or a "3D printer" to form the custom implant.

Where a CNC machine is used, the custom implant is preferably cut from the HPC after it has achieved sufficient hardness. For 3D printing, the HPC is used before it has hardened, when it is still in a sufficiently moldable form. In embodiments, the methods comprising 3D printing may include any of fused filament fabrication (FFF), fused deposition modeling (FOM), steriolithography, and gel mediums (with or without granules) where the gel medium allows the material extruder to pass through a contained gel matrix while extruding the formulation into the desired shape or configuration without breaking the extruder or allowing the extruded formulation to lose its desired shape. Gel matrices have been shown to be particularly helpful in 3D printing of flowable polymeric materials as they have an ability to "self-heal" locally and rapidly around the moving printing needle and extruded materials, essentially trapping the extruded materials in their desired shape configuration. For final implantation of these custom implant materials, any unreacted components may further serve to bond the custom implant material to the anatomical location that is to receive the implant. In accordance with the use of an HPC custom implant, it is understood that additional HPC material may be prepared and used to provide additional fixation for the custom implant and/or to augment the shape or configuration of the custom implant.

In embodiments, the custom HPC implant may be in a form of a disc, plate, wrap, tape, cuff, pin, rod, barb, anchor, screw, spacer, facet dowel, shim, or interbody cage.

Re-Approximation of Adjacent Bone Fragments

After reduction of adjacent cut or fractured bone, i.e., a procedure to restore the fracture or dislocation to the correct alignment, the restored alignment is typically stabilized using plates and/or metallic screws, tines, rods, etc. If the plate is made of a non-resorbable material, a second surgical procedure is required to remove it.

The present disclosure provides improved methods for re-approximation of adjacent bone fragments to create a restored alignment and stabilize the fracture line.

In the methods for reapproximation of cut or fractured bone, the HPC may be applied to one or both faces of the severed bone, or it may be applied between the two faces of the severed bone. In either case, when the adjacent bone fragments are brought together, the HPC serves initially as an adhesive to hold them in place. Unlike traditional tissue adhesives, the HPC rapidly cures into a solid form, providing the superior stabilization typically found only with a cement or metallic hardware. In addition, the restored alignment may be further stabilized by forming a second portion of HPC into a ribbon or cuff and wrapping the ribbon or cuff around the circumference of the reduced fracture line. Even further stabilization may be achieved by pressing additional portions of HPC into each of two or more drill holes located adjacent and opposite each other across the fracture line so as to substantially fill each hole with HPC, thereby providing the type of stabilization usually achieved only with a metal anchor, tine, screw, or similar fixture.

These methods may be adapted, for example, to repair fractured rib bones and long bones as shown in FIG. 1A, as well as for sternal closure as described below. FIG. 1A depicts methods for the repair of fractured rib and long bones by applying the HPC between the fractured bones (110), packing it into the hollow of the rib bone (120) like a facet dowel, wrapping the HPC formed into a ribbon or cuff around the circumference of the reduced fracture line (130), and by pressing the HPC into adjacent drill holes across the fracture line in the manner of an anchor, screw, or tine (140). This example illustrates the versatility of the HPC material.

Accordingly, in embodiments, the disclosure provides a method for re-approximation of adjacent cut or fractured bone. In embodiments, the method comprises intraoperatively mixing two or more reactive putties as described here at a suitable time during the procedure to form a first portion of HPC. In embodiments, the method further comprises applying a first portion of HPC between the two faces of the severed bone, or to one or both faces of the severed bone, or any combination of the foregoing, prior to reapproximation. In embodiments, the method further comprises forming a second portion of HPC into a ribbon or cuff and wrapping the HPC ribbon or cuff around the circumference of the reduced fracture line. In embodiments, the method further comprises pressing additional portions of HPC into each of two or more drill holes adjacent to each other on opposing sides of the reapproximation, further stabilizing it in the manner of an anchor, tine, or screw. In embodiments, the HPC replaces the need for other surgical adhesives and cement materials such that the method is performed without additional adhesives and/or cements made from non-HPC materials. In embodiments, the methods are performed without additional plates, rods, anchors, screws, and tines formed from non-HPC materials.

Method for Sternal Closure

Secure sternal closure is necessary following cardiac surgery in which a median sternotomy had been performed to access the heart. Stainless steel wire cerclage closure of the sternotomy is the current standard of care but this technique can result in complications such as pain, infection, and delayed healing secondary to physical sternal dislocation caused by forces such as coughing. The present disclosure provides improved methods for sternal closure that reduce the risk of infection while providing a stable closure that is both resistant to dislocation by external forces (e.g., coughing) and promotes bone healing.

Figure 1B:
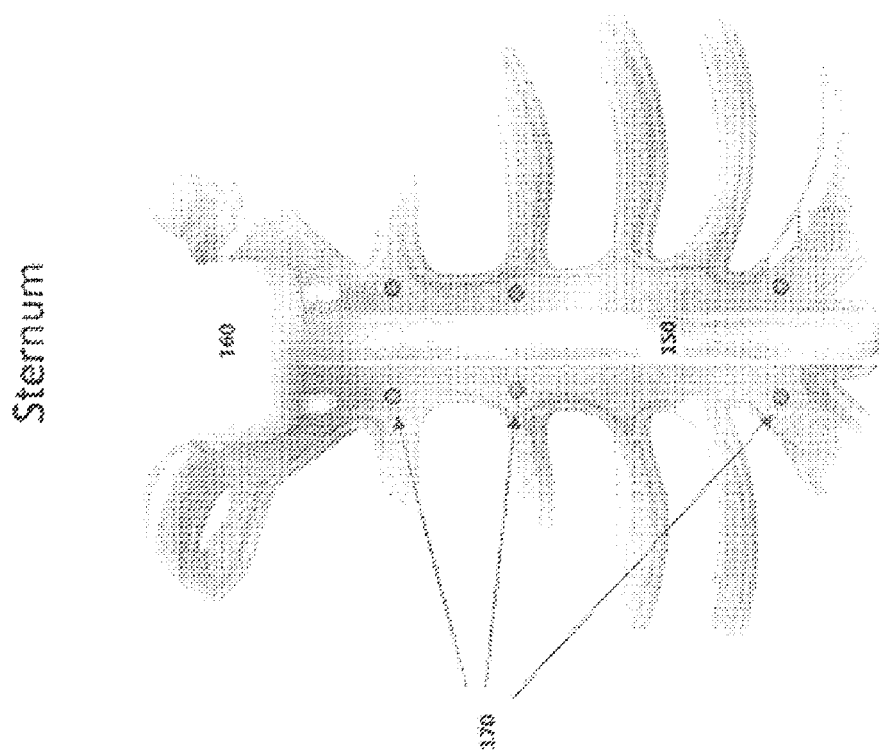

In embodiments of the methods for sternal closure described herein, the HPC is mixed intraoperatively at a suitable time during the operation prior to sternal closure. Once the individual putties have been mixed to form the HPC, the HPC may be separated into multiple portions of suitable size for application to the sternum at multiple points. For example, a first portion may be applied between the cut pieces of bone, or it may be applied separately to one or both cut edges of the sternum. The cut sternum is then reapproximated and the HPC material serves both as an adhesive and a cement, as described above. A second portion of HPC may be formed and applied as a ribbon or tape across the rejoined surface of the sternum so as to stabilize the fracture line. In addition, a third portion of the HPC may be pressed into one or more drill holes, for example, pairs of drill holes situated adjacent to each other on opposing sides of the reapproximation, further stabilizing it in the manner of an anchor, tine, or screw. In addition, a portion of the HPC material may be formed into a rod and connected to the HPC material filling the drill holes for yet further stabilization. FIG. 1B illustrates methods for reapproximating a cut sternum using the HPC by applying the HPC to the edges of the cut sternum across its longitudinal length (150), across the reapproximated surface of the sternum like a plate or tape (160), and pressed into adjacent drill holes across the fracture line (170) in the manner of an anchor, screw, or tine.

Accordingly, in embodiments, the disclosure provides a method for sternal closure. In embodiments, the method comprises intraoperatively mixing two or more reactive putties as described here at a suitable time during the procedure to form a first portion of HPC. In embodiments, the method comprises applying the first portion of the HPC between the two faces of the cut sternum, or to one or both faces of the cut sternum, or any combination of the foregoing, prior to re-approximation. In embodiments, the method further comprises applying a second portion of HPC across the approximated surface of the sternum so as to cover the reapproximated region. In embodiments, the method further comprises pressing further portions of HPC into each of two or more drill holes so as to substantially fill each drill hole. In embodiments, a further portion of HPC may be formed into rods which are joined to the HPC material pressed into the drill holes in order to further stabilize the fracture line.

Bone Plate

After reduction of adjacent cut or fractured bone, i.e., a procedure to restore the fracture or dislocation to the correct alignment, the restored alignment may be stabilized by securing a bone plate, typically made of metal, across the fracture line using metallic screws. The present disclosure provides an improved method for stabilizing a restored alignment in lieu of using a bone conventional plate and optionally also in lieu of using conventional screws, tines, and other fixtures that would have been need to secure the plate in place. The methods described here may be adapted for example, to repair cranial fractures and to secure a cranial flap.

Figure 2:
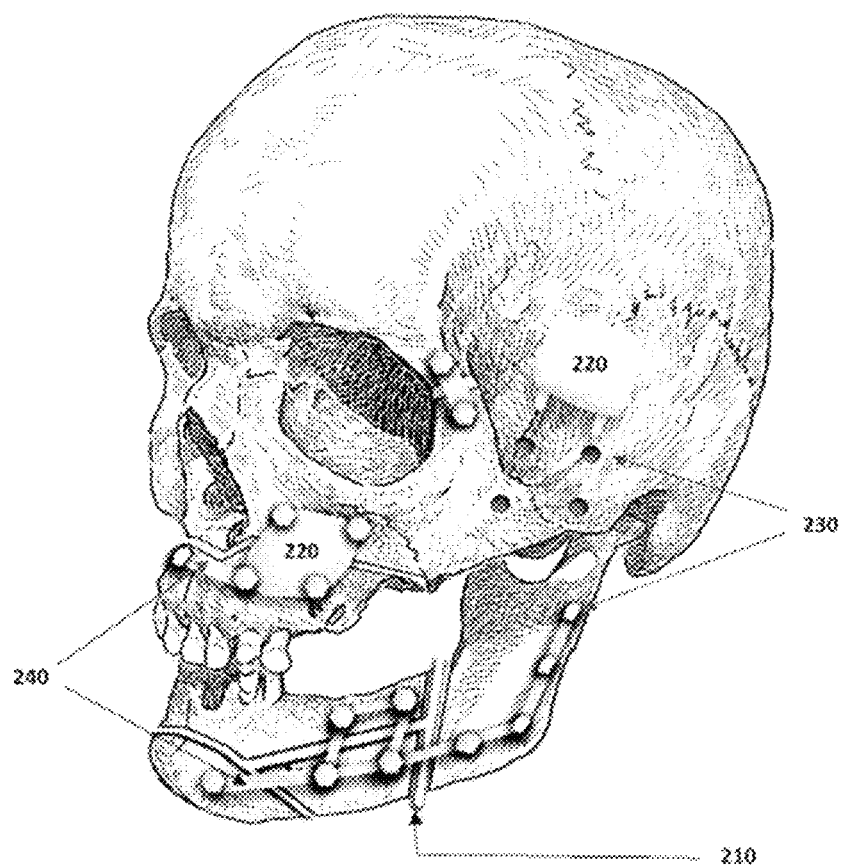
FIG. 2 is a schematic showing a perspective view of a skull depicting methods for repair of cranial fractures by applying the HPC between bone fragments (210), across reapproximated surfaces like a plate or tape (220), pressed into adjacent drill holes across the fracture line (230), and formed into rods (240) to further stabilize the fracture line.

FIG. 2 illustrates methods for repair of cranial fractures by applying the HPC between bone fragments (210), across reapproximated surfaces in the form of a plate or tape (220), pressed into adjacent drill holes across the fracture line to stabilize the fracture line in the manner of an anchor, screw, or tine (230), and formed into rods (240) which are joined to the material pressed into the drill holes in order to further stabilize the fracture line.

Figure 3:
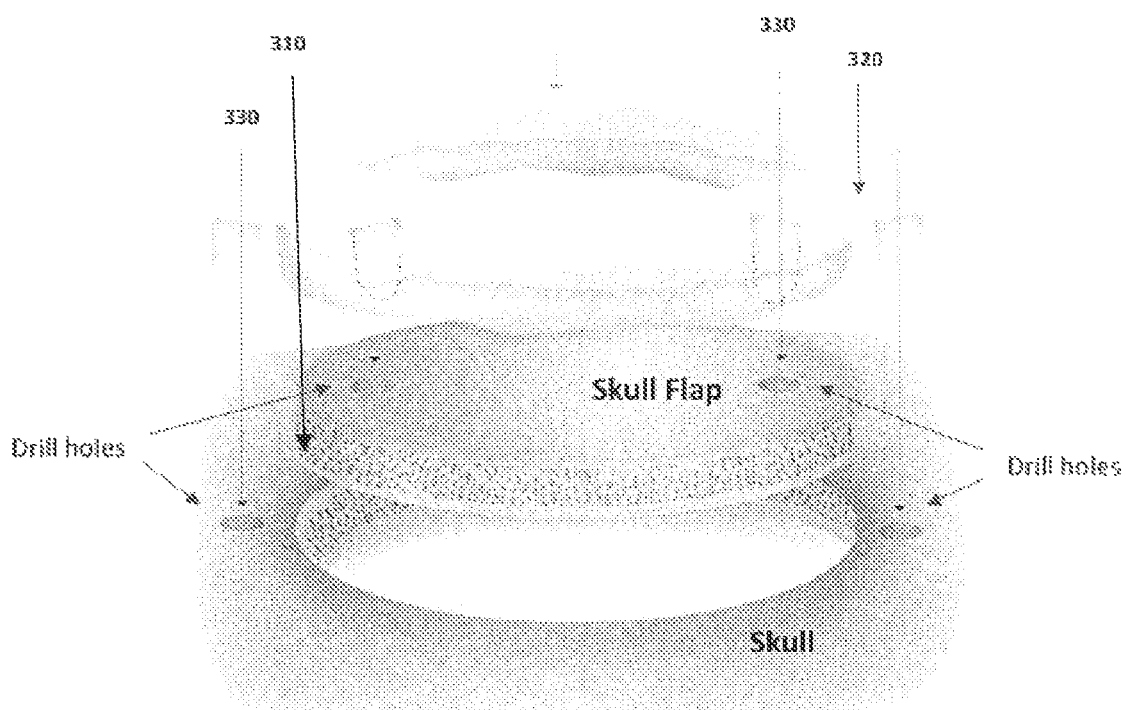
FIG. 3 is a schematic showing a perspective view of a cranial flap depicting methods for securing a cranial flap by applying the HPC between the circumference of the skull and flap (310), across the reapproximated surface of the skull and flap in the form of a plate or tape (320), and pressed into adjacent drill holes across the fracture line (330).

FIG. 3 illustrates methods for securing a cranial flap by applying the HPC between the circumference of the skull and flap (310), across the reapproximated surface of the skull and flap like a plate or tape (320), and pressed into adjacent drill holes across the fracture line in the manner of an anchor, screw, or tine (330).

Accordingly, in embodiments, the disclosure provides a method for stabilizing a restored alignment. In embodiments, the method comprises intraoperatively mixing two or more putties of a composition described here at a suitable time during the procedure to form a first portion of HPC. In embodiments, the first portion of HPC may be applied across the surface of a restored alignment, for example across the surface of a cranial flap. In embodiments, the method comprises pressing further portions of HPC into each of two or more drill holes situated adjacent to each other on opposing sides of the reapproximation, further stabilizing it in the manner of an anchor, tine, or screw. In embodiments, the method comprises applying additional portions of HPC to each face of the fracture or dislocation before restoring the bone to its correct alignment. In embodiments, the method further comprises drilling one or more holes into the hardened HPC after its application across the restored alignment and pressing further portions of the HPC into each of the drill holes so as to substantially fill each drill hole and further stabilize the fracture line.

Bone Wrap/Tape/Cuff

In some surgical procedures, after reduction of cut or fractured bone, an external orthopedic cast is used to stabilize and hold the bone in place until the cut or fracture has healed sufficiently. Such casts typically take the form of a plaster or fiberglass shell externally encasing the area to be stabilized. The disclosure provides methods for applying an internal orthopedic cast after reduction of cut or fractured bone that provides superior stability and may reduce or eliminate the need for an external cast.

Figure 4:
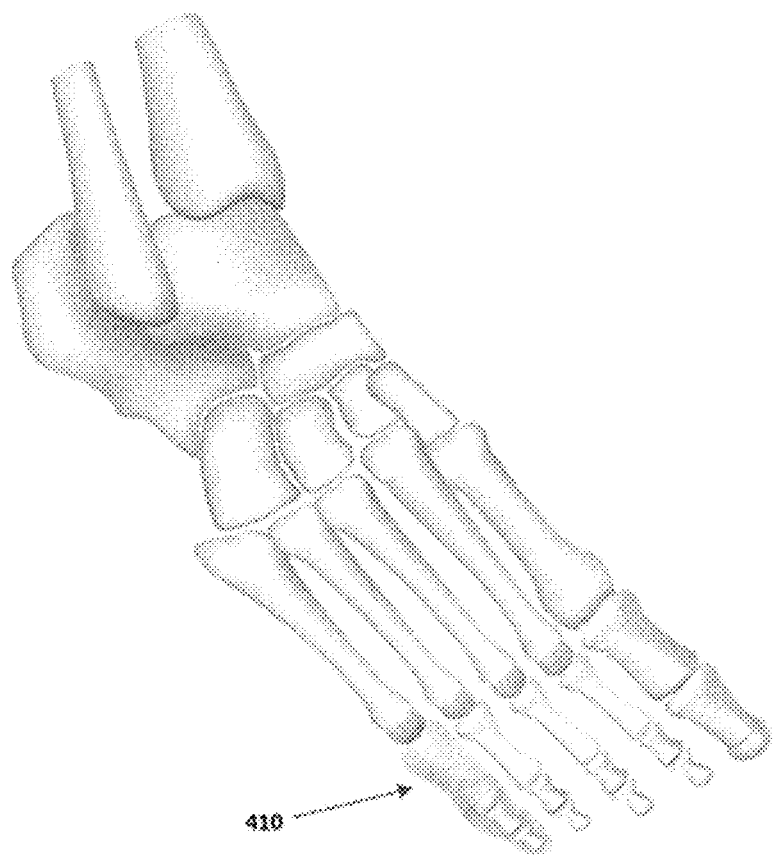
FIG. 4 is a schematic showing the repair of fractured short bones. A perspective view of the bones of the foot depicting methods for repair of fractured toe bone by wrapping (410) the HPC around the fragmented bones.

FIG. 4 depicts an exemplary method which is adapted for repair of a fractured toe bone by wrapping the HPC around the fragmented bone. In this way the HPC serves as a binder and a spacer, as well as acting as an adhesive holding the bones together and finally curing into a solid form that provides the stability of an orthopedic cast.

Accordingly, in embodiments, the disclosure provides a method for applying an internal orthopedic cast. In embodiments, the method comprises intraoperatively mixing two or more reactive putties as described here to form a first portion of HPC, stretching the HPC into the form of a ribbon or cuff, and wrapping the HPC ribbon or cuff around the circumference of the fractured bone to provide an internal orthopedic cast.

Spinal Fusion

Spinal fusion techniques seek to fuse together adjacent vertebrae into a single, solid bone. One method is referred to as interbody fusion and involves removing the intervertebral disk and replacing it with a metal, plastic, or bone "spacer" or "cage" implanted between the two adjacent vertebrae. The area of the spine surrounding the cage is typically stabilized with metal screws, plates, and rods. The present disclosure provides methods of interbody fusion which do not require metal screws, and may further be adapted to avoid the use of metal plates, rods, and cages.

Figure 5:
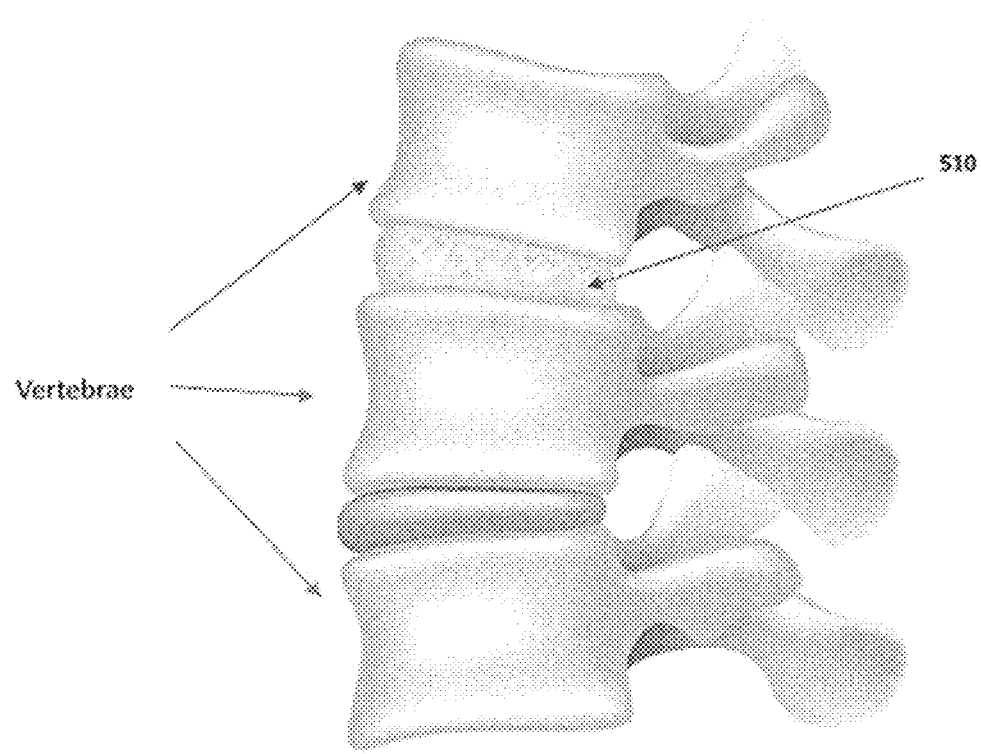
FIG. 5 is a schematic showing a perspective view of a portion of spine including three vertebrae and associated transverse processes and depicting methods for spinal fusion using the HPC as an interbody cage (510).
Figure 6:
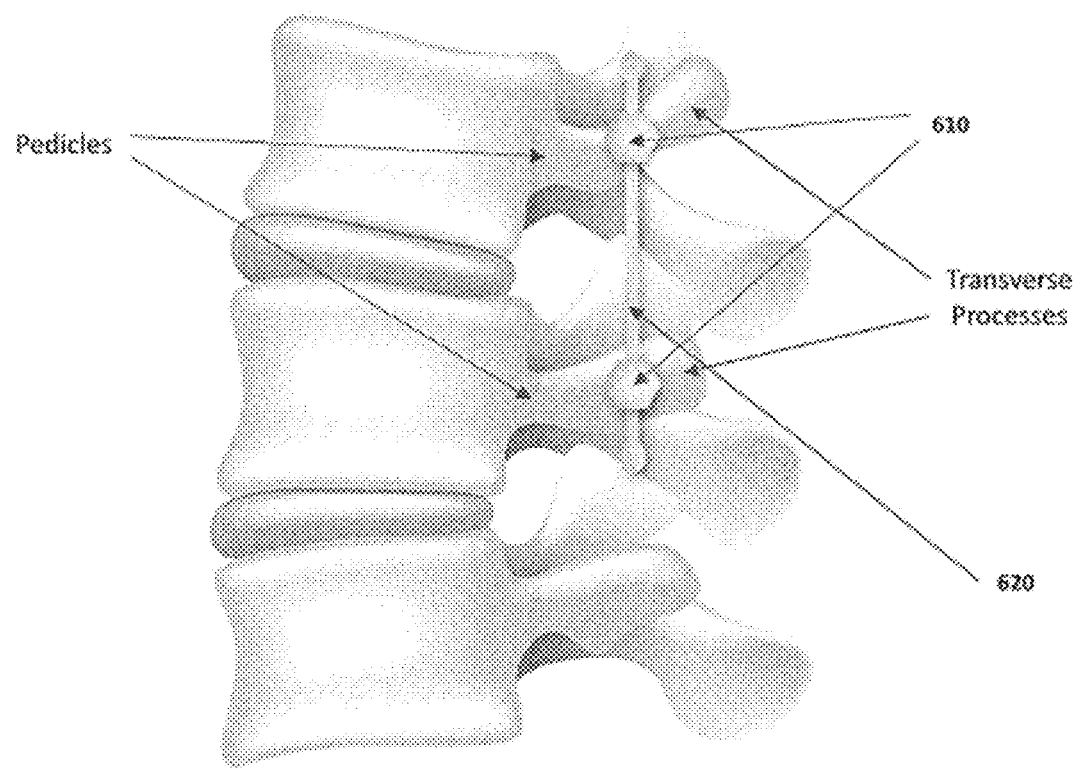
FIG. 6 is a schematic showing a perspective view of a portion of spine including three vertebrae and associated transverse processes and depicting methods for spinal fusion using the HPC applied to spinal pedicles (610) and across transverse processes (620) for fixation.

FIG. 5 illustrates the use of the HPC as a spacer or cage inserted between two vertebrae. FIG. 6 illustrates the use of the HPC applied to spinal pedicles (610) and across transverse processes (620) for fixation.

Accordingly, in embodiments, the disclosure provides methods for interbody fusion comprising intraoperatively mixing two or more reactive putties as described here to form a first portion of HPC. In embodiments, the methods comprising inserting the HPC into the space previously occupied by an intervertebral disk, thereby forming an HPC spacer or cage. In embodiments, the method further comprises drilling one or more holes into the HPC spacer or cage and introducing one or more of an autograft material, an allograft material, and a bone substitute material into the one or more holes of the HPC spacer or cage. In embodiments, the method further comprises applying a second portion of HPC to two or more spinal pedicles adjacent to the HPC spacer to form two or more HPC anchor points on the spinal pedicles and either stretching a further portion of HPC between the anchor points thereby connecting the anchor points, or positioning a rod between the anchor points and pressing the rod into the HPC anchor points.

Re-Approximation of Bone Fragments

In some circumstances, it is necessary to re-approximate a piece of dislodged or cut bone into a bone void. Standard procedures utilize an adhesive or glue that may or might not be bioabsorbable and/or biodegradable and may stabilize the reapproximated bone with a plate or tape, and/or with anchors, tines, or screws. The present disclosure provides an improved process which can be adapted to avoid any or all of these fixation devices and advantageously replace them with HPC.

Figure 7:
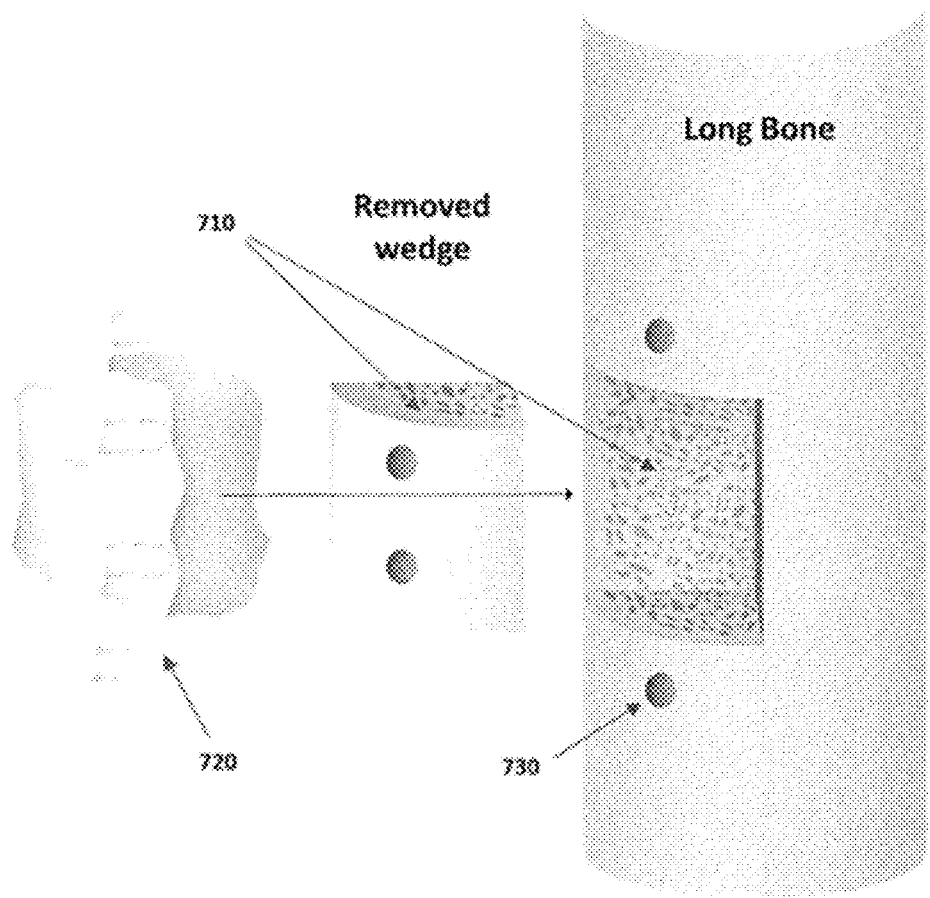
FIG. 7 is a schematic showing a perspective view of along bone containing a removed wedge of bone depicting methods for reapproximation of bone fragments using the HPC applied to the surfaces of the bone fragment and/or into the bone void (710), across the reapproximated surface (720) and pressed into drill holes (730).

FIG. 7 illustrates the various uses of HPC in a method for reapproximation of bone fragments. As shown in the figure, the HPC may be applied to the surfaces of the bone fragment and/or bone void, acting as an adhesive and cement when the surfaces are reapproximated. In addition, the HPC may be applied across the reapproximated surface in the form of a plate or tape, and/or pressed into drill holes situated adjacent to each other on opposing sides of the reapproximation, further stabilizing it in the manner of an anchor, tine, or screw.

Accordingly, in embodiments, the disclosure provides methods for re-approximation of a piece of cut or fractured bone. In embodiments, the method comprises intraoperatively mixing two or more reactive putties as described here to form a first portion of HPC. In embodiments, the methods comprise applying the first portion of HPC between the internal face or faces of the cut or fractured piece of bone, and/or to the exposed surface of the bone void into which the bone piece is to be placed; and pressing the bone piece into the bone void. In embodiments, the method further comprises applying a further portion of HPC across the surface of bone defined by the fracture lines. In embodiments, the method further comprises pressing further portions of HPC into each of two or more drill holes situated adjacent to each other on opposing sides of the reapproximation, further stabilizing it in the manner of an anchor, tine, or screw.

Stabilization of Hardware

The present disclosure provides methods for stabilizing surgical hardware generally. For example, the surgical hardware can be stabilized either by applying a portion of HPC between the surface of a bone and the joint hardware, by pressing a portion of HPC into a drill hole or other void prior to inserting the surgical hardware, e.g., an interbody cage or spacer, or an anchor, tine, or screw, and/or by applying a portion of HPC across the surface of the joint hardware after it has been affixed to the bone.

In some circumstances, it is necessary to create a shim to help stabilize a press fit joint replacement, due to localized bone deficits or a mismatch between hardware and bone geometry. Standard procedures simply utilize the press fit joint hardware alone. In an embodiment, the disclosure provides a method for stabilization of surgical hardware comprising intraoperatively mixing two or more reactive putties as described here to form a first portion of HPC, optionally dividing the HPC into one or more additional portions, and applying a portion of HPC between the internal surface of an intramedullary long bone space and a piece of joint hardware.

In embodiments, the disclosure provides a method for stabilization of surgical hardware comprising applying a portion of HPC to the bone surface, directly onto the joint hardware or to both areas.

In embodiments, the disclosure provides a method for stabilization of surgical hardware comprising filling a hole produced by tapping or drilling with a portion of HPC followed by pressing or screwing the surgical hardware into the HPC. The surgical hardware may be, for example, an anchor, tine, or screw.

Cartilage Repair

In embodiments, the HPC may be used in cartilage repair. For example, the HPC may be used to reshape a joint surface otherwise occupied by cartilaginous tissue. In embodiments, the HPC is used to plug a hole or fill a void in cartilaginous tissue. In embodiments, the HPC forms a spacer between adjacent cartilaginous tissues.

Examples of Reactive Putties and HPC Materials

The following provides non-limiting examples of exemplary reactive putties and HPC materials for use in the surgical methods described here, as well as some examples whose properties were not suitable, for comparison.

Table 1 below shows specific, non-limiting examples of reactive putties that form polyurethane/urea-based HPC materials. In each of the examples of Table 1, the isocyanate and polyol components are in the form of a prepolymer. The putties were formed by mixing a liquid isocyanate with a polyol and/or polyamine solution, and optionally as indicated in the table, adding a particulate component in the form of particulate calcium salts in amounts sufficient to establish suitable handling properties. For each, ALD was used as the isocyanate component but other suitable isocyanates may also be used including, for example, hexamethylene diisocyanate, toluene diisocyanate, a lactylglycolyl bridged diisocyanate, and lysine diisocyante. The polyol component used in the examples below consisted of polycaprolactone triol (molecular weight=400 KDa) and 1,5-pentane dial in a 9:1 molar ratio, respectively. Other suitable polyols may be used, for example, polypropyleneglycoltriol, and 1.4 butane diol. Where a polyamine was used in the examples below, it was a polyetheramine (Jeffamine D-400). Other suitable polyamines may be used, for example 1,4-butanediamine and hexamethylenediamine.

Generally, the use of prepolymers is preferred, since it allows control of mechanical properties as well as set time and can also be used to reduce the heat produced by the setting reaction, as discussed above.

Examples 1-3 utilize multi-putty compositions in which the optional particulate material is omitted. These examples illustrate the optimal ranges for the isocyanate and polyol/polyamine components of each putty that are needed to form putties with suitable handling properties in the absence of a particulate component.

Examples 4-8 illustrate multi-putty compositions having a particulate component in which hydroxyapatite and beta tricalcium phosphate particles in a size range of 250-630 micrometer diameter are combined with smaller beta tricalcium phosphate particles to form optimum putties. Examples 5-7 include polyamines in the polyol/polyamine component. Example 8 provides an illustration of a "fast setting" HPC.

Examples 9 and 10 exemplify single putty compositions which may be molded or shaped into an appropriate implant and placed in situ to harden by reacting with water at the site of implantation, as discussed infra in connection with the "moisture cure" embodiment. The examples show that sufficient amounts of the isocyanate component must be present in order to form a hardened material in situ.

TABLE 1

Reactive putties and polyurethane/urea-based HPC materials

| # | Putty | Isocyanate and Polyol/polyamine components (wt %) | Particulate (wt %) | Reactive Putty Observations | HPC Observations |
|---|---|---|---|---|---|
| 1 | A | ALD (75%) + Polyol (25%) | None | Excellent handling properties | Workable for about 10 min.; appeared fully hardened after 24 hrs; final putty was hard and stiff. |
|   | B | ALD (60%) + Polyol (40%) | None | Excellent handling properties | |
| 2 | A | ALD (95%) + Polyol (5%) | None | Poor handling properties, sticky | Difficult to mix, sticking to gloved hands. Fully hardened after 24 hrs; Final putty was hard and stiff. |
|   | B | ALD (20%) + Polyol (80%) | None | Poor handling properties, sticky | |
| 3 | A | ALD (60%) + Polyol (40%) | None | Poor handling properties, stiff | Unable to mix, putty A too stiff. |
|   | B | ALD (60%) + Polyol (40%) | None | Excellent handling properties | |
| 4 | A | ALD (36%) + Polyol (3%) | HA/TCP (250-630 μm) (51%) + β-TCP (5 μm) (5%) | Excellent handling properties | Workable for about 10 min.; appeared fully hardened after 24 hrs; final putty was hard and stiff. |
|   | B | ALD (11%) + Polyol (9%) | HA/TCP (250-630 μm) (20%) + β-TCP (5 μm) (60%) | Excellent handling properties | |
| 5 | A | ALD (36%) + Polyol (3%) | HA/TCP (250-630 μm) (51%) + β-TCP (5 μm) (5%) | Excellent handling properties | Workable for about 8 min.; appeared fully hardened after 24 hrs; final putty was hard and stiff |
|   | B | ALD (11%) + Polyol (7%) + Polyamine (2%) | HA/TCP (250-630 μm) (20%) + β-TCP (5 μm) (60%) | Excellent handling properties | |
| 6 | A | ALD (33%) + Polyol (7%) | HA/TCP (250-630 μm) (55%) + β-TCP (5 μm) (5%) | Excellent handling properties | Workable for about 10 min.; appeared fully hardened after 24 hrs; final putty was hard and stiff. |
|   | B | ALD (11%) + Polyol (7%) + | β-TCP (5 μm) (5%) | Excellent handling properties | |
| 7 | A | ALD (35%) + Polyamine (5%) | HA/TCP (250-630 μm) (51%) + β-TCP (5 μm) (9%) | Excellent handling properties | Workable for about 8 min.; appeared fully hardened after 24 hrs; final putty was hard and stiff. |
|   | B | ALD (11%) + Polyol (7%) + Polyamine (2%) | HA/TCP (250-630 μm) (20%) + β-TCP (5 μm) (60%) | Excellent handling properties | |
| 8 | A | ALD (35%) + Polyamine (5%) | HA/TCP (250-630 μm) (51%) + β-TCP (5 μm) (9%) | Excellent handling properties | Workable for about 2 min.; appeared fully hardened |

TABLE 1-continued

Reactive putties and polyurethane/urea-based HPC materials

| # | Putty | Isocyanate and Polyol/polyamine components (wt %) | Particulate (wt %) | Reactive Putty Observations | HPC Observations |
|---|---|---|---|---|---|
|   | B | ALD (11%) + Polyol (7%) + Polyamine (2%) | HA/TCP (250-630 μm) (20%) + β-TCP (5 μm) (60%) | Excellent handling properties | after 10 min; final putty was hard and stiff. |
| 9 | — | ALD (36%) + Polyol (3%) | HA/TCP (250-630 μm) (51%) + β-TCP (5 μm) (9%) | Excellent handling properties | Submerged in saline. Fully hardened after 24 hours through formation of polyurethane urea. |
| 10 | — | ALD (6%) + Polyol (34%) | HA/TCP (250-630 μm) (41%) + β-TCP (5 μm) (19%) | Excellent handling properties | Submerged in saline. No hardening. |

β-TCP = beta tricalcium phosphate
HA/TCP = Hydroxyapatite/beta tricalcium phosphate

TABLE 2

Reactive putties and HPC materials based on non-polyurethane technologies

| # | Putty | Reactive components (wt %) | Additive (wt %) | Reactive Putty Observations | HPC Observations |
|---|---|---|---|---|---|
| 1 | A | 7% Carboxymethyl cellulose solution (Negatively charged polyanionic polymer) | None | Aqueous putty | Forms a semi-solid hydrogel putty |
|   | B | 7% Chitosan hydrochloride solution (Positively charged polycationic polymer) | None | Aqueous putty |   |
| 2 | A | Same as 1A | 25% Calcium phosphate powder | Aqueous putty | Forms a semi-solid hydrogel putty |
|   | B | Same as 1B | 25% hydroxyapatite powder | Aqueous putty |   |
| 3 | A | Same as 1A | None | Aqueous putty | Forms a semi-solid hydrogel putty |
|   | B | Same as 1B | 2% lidocaine HCl | Aqueous putty |   |
| 4 | A | 70-30% polyisobutyl cyanoacrylate 0.1-1% hydroquinone 0.25-0.5% sulfur dioxide | None | Must be protected from moisture | Not hand moldable |
|   | B | 97-99% polyisobutyl cyanoacrylate 0.1-3% benzoyl peroxide and/or ferric chloride | None | Must be protected from moisture |   |
| 5 | A | 60-80% triglycidal-p-amino phenol 20-40% micronized polyvinyl pyrrolidone or of micronized calcium phosphate | None | Hand moldable putty | While reacting, the combined putties may be used as a nonabsorbable cement for hard tissue such as fractured or as a hemostat to control bleeding bone. |
|   | B | 60-80% dicyclohexyl amine 20-40% micronized hydroxyapatite | 5% tocopheryl acetate. 2% antimicrobial agent 10% fructose crystals | Hand moldable putty |   |
| 6 | A | Same as 5A |   | Hand moldable putty | Composition provides a resorbable epoxy polymer with hydrolysable ester linkages in Putty B |
|   | B | 60-80% of a comonomer of the diglycidal ester of ethylene glycol-beta-hydroxypropionate 20-40% of a thickener comprised of micronized calcium phosphate | 10% sugar fibers (cotton candy) | Hand moldable putty |   |
| 7 | A | 35% polyethyleneglycol monostearate 10% polyethylene glycol 30% tetracalcium phosphate 20% phosphoserine 5% dry phosphate buffer precursor powder |   | Hand moldable putty |   |
|   | B | 35% polyethyleneglycol monostearate 30% polyethylene glycol 30% micronized polyglycolic | Optional: 0.2% D&C Violet 2 | Hand moldable putty |   |

TABLE 2-continued

Reactive putties and HPC materials based on non-polyurethane technologies

| # | Putty | Reactive components (wt %) | Additive (wt %) | Reactive Putty Observations | HPC Observations |
|---|---|---|---|---|---|
| | | acid (for absorbable cements) or, 30% micronized polyethyleneterephthalate (for nonabsorbable cements) 5% dry phosphate buffer precursor powder | | | |
| 8 | A | 30% finely powdered $KH_2PO_4$ (monopotassium phosphate) 15% finely powdered calcined MgO (magnesium oxide) 45% polyethyleneglycol monostearate 10% triacetin | | Hand moldable putty | |
| | B | 20% finely powdered hydroxyapatite 20% finely powdered sucrose 50% polyethyleneglycol monostearate 10% triacetin | Optional: 0.2% D&C Violet 2 | Hand moldable putty | |

Surgical Kits and Packages

Also provided is a surgical kit or package comprising any of the components described herein.

As a practical matter, during use of a settable composition in surgery, freshly made material may be required at widely spaced points in time. If the material is not mixed just before use, its moldability, uniformity, and adherence to the surfaces to which it is applied will be diminished. In this context, the adhesive nature of the material is a function of its uncured state. In some embodiments, the composition as it cures bonds to the tissue at the site of implantation, for example bone tissue. And if the material is compounded too early, it may set before it can be applied. In such a state, it will be insufficiently moldable, insufficiently adhesive, and unsuitable for use.

The surgical kits and packages described herein provide a solution to this problem by providing the availability of freshly made settable material at different times during a surgical procedure.

In embodiments, the present disclosure provides a container comprising two or more compartments, each compartment containing an amount of a component. Where the container comprises multiple sets of components, the compartments are adapted such that each set can be removed without disturbing the other sets in the package. If the components are sterile, the container is adapted such that each set of components can be aseptically removed without compromising the sterility of the remaining sets. For example, the separate compartments may form the lower part of a vacuum-formed container with an upper peelable film. The construction of the container allows for the removal of a single set of components from their respective compartments just before use. The components, thus exposed, then are removed from the container by a gloved finger or by using an instrument and are kneaded together until homogenous to form a single composition for use. The composition thus formed will initially be in a moldable form. In embodiments, the composition is in the form of a putty, and the components of each set are also in the form of putties. As the composition sets, it hardens into a solid form. When needed, the next set of compartments in the unit is exposed by peeling down their covering film and kneading the newly exposed putties together until homogeneous and ready for surgical use. In embodiments, the container comprises pairs of compartments and the set of components is a pair. In embodiments, the container comprises 2 to 12 sets (i.e., 2, 3, 4, 5, 6, 7, 8, 9, 10, 11, or 12 sets) of components.

The compartments of the package may be, for example, in the form of a depression or well, or the compartments may comprise walls made of a flexible material having any shape, or an amorphous shape. In embodiments in which the package comprises multiple pairs of putties, the package may contain any desired number of putty pairs. In embodiments, the package consists of 2, 4, 8, 10, 12, or more putty pairs. In embodiments, perforations may be placed between pairs to facilitate removal of a pair before or after opening.

In embodiments, the package comprises separate compartments or wells of a lower, vacuum-formed container with an upper peelable film, designed to allow a single set of putties to be removed from a single set of compartments as needed, e.g., just before use during surgery. In embodiments, the set consists of two and a single package contains from 2 to 12 or more sets (i.e., 2, 3, 4, 5, 6, 7, 8, 9, 10, 11, 12, or more sets) of putties.

In embodiments, the package comprises a syringe component. In embodiments, the syringe component is a single syringe pre-loaded with measured amounts of a set of putties in separate internal compartments of the syringe such that when the syringe plunger is depressed, amounts of each component are dispensed or extruded from the syringe to form a composition that will harden into a final solid (cured) form over a period of time at room temperature or body temperature. In embodiments, the syringe component comprises two or more syringes, each pre-loaded with one component of a set. In embodiments, the set consists of two components.

In other embodiments, the package comprises separate flexible compartments within a flexible plastic container, each compartment having a seal that, when disrupted, allows the contents of the compartments to mix together into a common flexible plastic compartment that is configured to allow mixing of the contents within the common flexible plastic compartment. In embodiments, the package is flexible enough to allow mixing by hand-kneading. In further embodiments, after mixing is complete, an orifice is cut into the container to allow removal of the mixed components.

In embodiments, the package comprises or consists of a heat sealed or heat sealable foil package. In embodiments, the package further comprises an outer envelope completely surrounding the package, and a desiccant. In embodiments, the outer envelope is a heat sealed, pinhole free foil package.

In embodiments, the package comprises a surface which is in contact with the components, said surface having a surface energy substantially equal to or less than the surface energy of the components, or both, such that the component does not adhere or adheres weakly to the surface. In embodiments, the surfaces of the package that are in contact with the components are coated with a surface having a surface energy substantially equal to or less than the surface energy of the components such that they do not adhere, or adhere weakly to, the surface. In embodiments, the surface is formed of a material selected from the group consisting of polytetrafluoroethylene (PTFE), silicone, polypropylene, polyethylene, and polystyrene.

In embodiments, a package has a shelf life of at least 1-2 years. In embodiments, the package has a shelf life of 6 months, 12 months, 18 months, 24 months, 36 months, or more.

As an aid to manipulating the components after extrusion from the syringe or syringes, or after removal from the packaging, the surgeon may employ a device having a pliable structure with an application surface having a surface energy substantially equal to or less than the surface energy of the composition such that the composition does not adhere or adheres very weakly to the device. The device is preferably in the form of a sheet. Suitable materials for forming the application surface include, for example, polytetrafluoroethylene (PTFE), silicone, polypropylene, polyethylene, and polystyrene. Such devices are described in US 2012/0035610, which is herein incorporated by reference.

EQUIVALENTS

Those skilled in the art will recognize or be able to ascertain using no more than routine experimentation, many equivalents to the specific embodiments described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present disclosure is not to be limited in scope by the specific embodiments described herein. Indeed, various modifications in addition to those described herein will become apparent to those skilled in the art from the foregoing description and accompanying figures. Such modifications are intended to fall within the scope of the appended claims.

What is claimed is:

1. A method for joining pieces of cut or fractured bone, the method comprising
   intraoperatively mixing two or more individual reactive putties to form a homogenous putty composition (HPC),
   dividing the HPC into two or more portions,
   applying a first portion of the HPC to the cut or fractured surface of at least one of the pieces of bone:
   (i) in multiple portions at a plurality of locations of the cut or fractured surface and interrupted by gaps; or
   (ii) as a single portion across substantially the entire length of the cut or fractured surface, and
   maintaining the pieces of cut or fractured bone in proximity to form a reduced fracture until the HPC has hardened and the reduced fracture remains fixed;
   wherein the method further comprises:
   (a) applying an additional portion of the HPC across the reduced fracture line in the form of a plate or tape;
   (b) pressing an additional portion of the HPC into each of two or more drill holes located opposite each other across the reduced fracture line, thereby substantially filling each drill hole; and/or
   (c) stretching an additional portion of the HPC into the form of a ribbon or cuff and wrapping the HPC ribbon or cuff around the circumference of the reduced fracture line.

2. The method of claim 1, further comprising compressing the pieces of cut or fractured bone together until the first portion of the HPC has hardened.

3. The method of claim 1, wherein the pieces of cut or fractured bone are maintained in proximity for about 2 to 5 minutes.

4. The method of claim 1, wherein the method further comprises shaping an additional portion of the HPC into a rod and joining each end of the rod to a portion of the HPC pressed into a drill hole.

5. The method of claim 4, wherein the method further comprises drilling a hole into the HPC material in the form of a plate or tape after the HPC has hardened.

6. The method of claim 1, wherein the bone is a long bone, a short bone, a flat bone, an irregular bone, or a sesamoid bone.

7. The method of claim 6, wherein the bone is a flat bone selected from a sternum, rib, scapula, or cranial bone.

8. The method of claim 7, wherein the bone is a rib and the method further comprises applying an additional portion of the HPC into the hollow of the rib bone.

9. The method of claim 6, wherein the irregular bone is a vertebrae.

10. The method of claim 9, wherein the method further comprises inserting an additional portion of the HPC into an intervertebral space to form a spacer or cage.

11. The method of claim 10, further comprising applying a second portion of the HPC to two or more spinal pedicles adjacent to the HPC spacer or cage to form two or more HPC anchor points on the pedicles and either stretching a further additional portion of the HPC between the anchor points or positioning a rod between the anchor points and pressing the rod into the anchor points, thereby connecting the anchor points.

12. A method for joining at least two pieces of fractured long or short bone, the method comprising:
   intraoperatively mixing together two or more individual reactive putties to form an HPC,
   dividing the HPC into at least two portions,
   applying a first portion of the HPC to the cut or fractured surface of at least one of the pieces of bone:
   (i) in multiple portions at a plurality of locations of the cut or fractured surface and interrupted by gaps; or
   (ii) as a single portion across substantially the entire length of the cut or fractured surface; and maintaining the at least two pieces of cut or fractured bone in proximity to form a reduced fracture until the HPC has hardened sufficiently to maintain the reduced fracture repair fixed,
   wherein the method further comprises:
   shaping a second portion of the HPC into the form of a ribbon or cuff and wrapping the HPC ribbon or cuff around the circumference of the reduced fracture line, pressing portions of the one or more additional HPCs into each of two or more drill holes located opposite each other across the reduced fracture line, thereby substantially filling each drill hole, shaping a portion of the one or more additional HPCs into a rod and joining each end of the rod to a portion of HPC pressed into a drill hole, or any combinations thereof.

13. The method of any one of claims 1 or 12, wherein the HPC comprises 20-30 wt % of a polyurethane or polyurethane urea copolymer, 60-75 wt % of a particulate material, and 4-10 wt % of one or more additive materials, wherein the first reactive putty comprises an isocyanate component and the second reactive putty comprises a polyol component, a polyamine component, or both a polyol component and a polyamine component, wherein each reactive putty independently further comprises an optional particulate component, and wherein the first reactive putty comprises prepolymer and free isocyanate and the second reactive polymer comprises prepolymer and free polyol, polyamine, or polyol and polyamine.

14. The method of claim 13, wherein, when the optional particulate component is present, the prepolymer is present in an amount of from about 2-10 wt % of each individual reactive putty.

15. The method of claim 14, wherein the prepolymer is present in an amount of about 5-7 wt % or about 3-8 wt % of each individual reactive putty.

16. The method of claim 13, wherein, when the optional particulate component is absent, the prepolymer is present in an amount of from about 15-50 wt % or about 20-50 wt % of each individual reactive putty.

17. The method of claim 13, wherein the particulate component comprises spherical particles of calcium phosphate in a size range of from about 1-700 microns mean diameter and a density in the range of 2-3 g/cm$^3$.

18. The method of claim 17, wherein the calcium phosphate particles consist of particles selected from one or more of tricalcium phosphate (TCP), tetracalcium phosphate, calcium pyrophosphate, hydroxyapatite, siliconized calcium phosphate, and a substituted calcium phosphate where the substitution is with magnesium, strontium, or silicate.

19. The method of claim 18, wherein the calcium phosphate particles consist of particles of tricalcium phosphate and hydroxyapatite.

20. The method of claim 17, wherein the particulate component comprises a ceramic material selected from substituted calcium phosphates, a glass, or bioglass.

21. The method of claim 13, wherein the particulate component comprises particles of calcium sulfate, bone, partially or fully demineralized bone matrix (DBM), mineralized bone, or combinations thereof.

22. The method of claim 21, wherein the particulate component comprises particles of bone in the form of demineralized bone, allograft bone, autogenous bone, or combinations thereof.

23. The method of claim 13, wherein the HPC comprises one or more additive materials selected from one or more of a carboxylic acid ester of glycerin, a divalent metal salt of a fatty acid, the acetic acid ester of tocopherol, an N-alkylpyrrolidone, or triethanolamine.

24. The method of claim 13, wherein the HPC comprises one or more additive materials comprises one or more therapeutic agent selected from the group consisting of an anti-cancer agent, an antimicrobial agent, an antibiotic, a local anesthetic or analgesic, a statin, and an anti-inflammatory agent.

25. The method of claim 13, wherein the HPC exhibits a stiffness in the range of about 4-6 millimeters for at least about 2 minutes after its formation when subjected to a penetrometer test using a force of about 50 grams applied for about 5 seconds.

26. The method of claim 13, wherein the HPC exhibits a stiffness in the range of about 0.2-0.4 millimeters about 15 minutes after its formation when subjected to a penetrometer test using a force of about 50 grams applied for about 5 seconds.

27. The method of claim 13, wherein the HPC is sterile.

28. The method of claim 13, wherein the HPC is fully or partially biodegradable, bioabsorbable under physiological conditions, or both fully or partially biodegradable and bioabsorbable under physiological conditions.

* * * * *

UNITED STATES PATENT AND TRADEMARK OFFICE
CERTIFICATE OF CORRECTION

PATENT NO. : 11,160,899 B2
APPLICATION NO. : 16/183221
DATED : November 2, 2021
INVENTOR(S) : Richard L. Kronenthal et al.

Page 1 of 1

It is certified that error appears in the above-identified patent and that said Letters Patent is hereby corrected as shown below:

In the Claims

At Column 54, Claims number 20 through 22, Lines 4 through 14, Should read:
-- 20. The method of claim 13, where in the particulate component comprises particles of calcium sulfate, bone, partially or fully demineralized bone matrix (DBM), mineralized bone, or combinations thereof.
21. The method of claim 20, wherein the particulate component comprises particles of bone in the form of demineralized bone, allograft bone, autogenous bone, or combinations thereof.
22. The method of claim 17, wherein the particulate component comprises a ceramic material selected from substituted calcium phosphates, a glass, or bioglass. --

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*